US012569198B2

(12) United States Patent
Chavoshi et al.

(10) Patent No.: US 12,569,198 B2
(45) Date of Patent: Mar. 10, 2026

(54) APPARATUS, SYSTEM AND METHOD FOR ELECTROMAGNETIC IMAGING

(71) Applicant: AIIMSENSE INC., Kitchener (CA)

(72) Inventors: Mohammad Chavoshi, Waterloo (CA); Atefeh Sadat Zarabadi, Waterloo (CA); Mohammad Mohammadirad, Tehran (IR)

(73) Assignee: AllmSense Inc., Kitchener (CA)

( * ) Notice: Subject to any disclaimer, the term of this patent is extended or adjusted under 35 U.S.C. 154(b) by 824 days.

(21) Appl. No.: 17/828,532

(22) Filed: May 31, 2022

(65) Prior Publication Data

US 2023/0014769 A1 Jan. 19, 2023

Related U.S. Application Data

(60) Provisional application No. 63/195,119, filed on May 31, 2021.

(51) Int. Cl.
A61B 5/00 (2006.01)

(52) U.S. Cl.
CPC .......... A61B 5/6814 (2013.01); A61B 5/0042 (2013.01); A61B 5/0055 (2013.01); *A61B 2562/043* (2013.01); *A61B 2562/046* (2013.01)

(58) Field of Classification Search
CPC ... A61B 5/6814; A61B 5/0042; A61B 5/0055; A61B 2562/043; A61B 2562/046
See application file for complete search history.

(56) References Cited

U.S. PATENT DOCUMENTS

| | | | |
|---|---|---|---|
| 9,072,449 | B2 | 7/2015 | Semenov |
| 9,320,451 | B2 | 4/2016 | Feldkamp et al. |
| 9,436,799 | B2 | 9/2016 | Mccoy et al. |
| 9,436,991 | B2 | 9/2016 | Campagna et al. |
| 9,456,757 | B1 | 10/2016 | Zheng |
| 9,471,748 | B2 | 10/2016 | Liu et al. |
| 9,645,207 | B2 | 5/2017 | Taracila et al. |
| 9,730,628 | B2 | 8/2017 | Iasemidis et al. |
| 9,924,873 | B2 | 3/2018 | Semenov |
| 10,197,657 | B2 | 2/2019 | Akhtari |
| 10,863,942 | B2 | 12/2020 | Gou |
| 10,898,152 | B1 | 1/2021 | Kim et al. |
| 10,925,568 | B2 | 2/2021 | Lu et al. |
| 10,952,613 | B2 | 3/2021 | Kim et al. |

(Continued)

FOREIGN PATENT DOCUMENTS

| | | |
|---|---|---|
| CN | 116893416 A | 10/2023 |
| EP | 1595205 B1 | 4/2018 |

(Continued)

OTHER PUBLICATIONS

Hussain et al., "HealthSOS: Real-Time Health Monitoring System for Stroke Prognostics," in IEEE Access, vol. 8, pp. 213574-213586 (2020), DOI: 1109/ACCESS.2020.3040437.

(Continued)

*Primary Examiner* — Dixomara Vargas
(74) *Attorney, Agent, or Firm* — Own Innovation; James W. Hinton; Caitlyn O'Flynn

(57) ABSTRACT

An electromagnetic (EM) tomography head scanner comprising an antenna chamber, a radio frequency and microwave circuit, a control and monitoring unit, and a signal processing unit and an artificial intelligence unit.

17 Claims, 26 Drawing Sheets

(56) References Cited

U.S. PATENT DOCUMENTS

| | | | |
|---|---|---|---|
| 11,250,601 | B2 | 2/2022 | Chen et al. |
| 11,412,933 | B2 | 8/2022 | Agrawal |
| 11,607,134 | B2 | 3/2023 | Semenov |
| 11,701,070 | B2 | 7/2023 | Landi et al. |
| 11,715,179 | B2 | 8/2023 | Zhang et al. |
| 11,715,211 | B2 | 8/2023 | Lovchinsky et al. |
| 11,756,160 | B2 | 9/2023 | Park et al. |
| 11,837,362 | B2 | 12/2023 | Lautenschlaeger |
| 11,928,859 | B2 | 3/2024 | Nouri et al. |
| 2003/0181804 | A1 | 9/2003 | Gagnon et al. |
| 2010/0056912 | A1 | 3/2010 | Urness et al. |
| 2010/0069744 | A1* | 3/2010 | Simpkin .............. A61B 5/0507 |
| | | | 600/425 |
| 2011/0320515 | A1 | 12/2011 | Mohammed |
| 2013/0185331 | A1 | 7/2013 | Conemac |
| 2014/0153796 | A1 | 6/2014 | Sundaran et al. |
| 2014/0155740 | A1 | 6/2014 | Semenov |
| 2014/0218230 | A1* | 8/2014 | Ostadrahimi ......... G01N 22/00 |
| | | | 342/179 |
| 2016/0092632 | A1 | 3/2016 | Zhou et al. |
| 2016/0278653 | A1 | 9/2016 | Clark et al. |
| 2016/0346562 | A1* | 12/2016 | Saitoh ...................... A61N 2/02 |
| 2017/0014637 | A1* | 1/2017 | Basser ..................... A61N 1/40 |
| 2018/0085026 | A1* | 3/2018 | Kaneko ................ A61B 5/0537 |
| 2019/0274578 | A1 | 9/2019 | Semenov |
| 2021/0272237 | A1 | 9/2021 | Fang et al. |
| 2022/0076819 | A1 | 3/2022 | Danial et al. |
| 2022/0079443 | A1 | 3/2022 | Abbosh et al. |
| 2022/0107378 | A1 | 4/2022 | Dey et al. |
| 2022/0192919 | A1 | 6/2022 | Wilson et al. |
| 2022/0365151 | A1 | 11/2022 | Hou et al. |
| 2023/0012014 | A1 | 1/2023 | Daks et al. |
| 2023/0267699 | A1 | 8/2023 | Zaslavsky et al. |
| 2023/0417852 | A1 | 12/2023 | Rothberg et al. |
| 2024/0008832 | A1 | 1/2024 | Chan et al. |
| 2024/0013909 | A1 | 1/2024 | Omar et al. |
| 2024/0038369 | A1 | 2/2024 | Yeleti et al. |
| 2024/0081939 | A1* | 3/2024 | Wasserman ............ G16H 50/50 |

FOREIGN PATENT DOCUMENTS

| | | | |
|---|---|---|---|
| WO | 2017125397 | A1 | 7/2017 |
| WO | 2018223178 | A1 | 12/2018 |
| WO | 2020047597 | A1 | 3/2020 |
| WO | 2022221297 | A1 | 10/2022 |

OTHER PUBLICATIONS

Cook et al., "Case Report: Preliminary Images From an Electromagnetic Portable Brain Scanner for Diagnosis and Monitoring of Acute Stroke," Front. Neurol., vol. 12, Article ID 765412. (2021) DOI:10.3389/fneur.2021.765412, 7 pages.

Xu et al., "Noninvasive and portable stroke type discrimination and progress monitoring based on a multichannel microwave transmitting-receiving system," Sci Rep 10, 21647 (2020). DOI: 10.1038/s41598-020-78647-x, 13 pages.

Zhao et al., " Twenty-four-hour real-time continuous monitoring of acute focal cerebral ischemia in rabbits based on magnetic inductive phase shift," BioMed Eng OnLine 19, 83 (2020). DOI: 10.1186/s12938-020-00829-5, 15 pages.

Ma et al., "Exploratory Study on the Methodology of Fast Imaging of Unilateral Stroke Lesions by Electrical Impedance Asymmetry in Human Heads," Hindawi Publishing Corporation, The Scientific World Journal, vol. 2014 (2014), Article ID 534012, DOI: 10.1155/2014/534012, 18 pages.

* cited by examiner

150

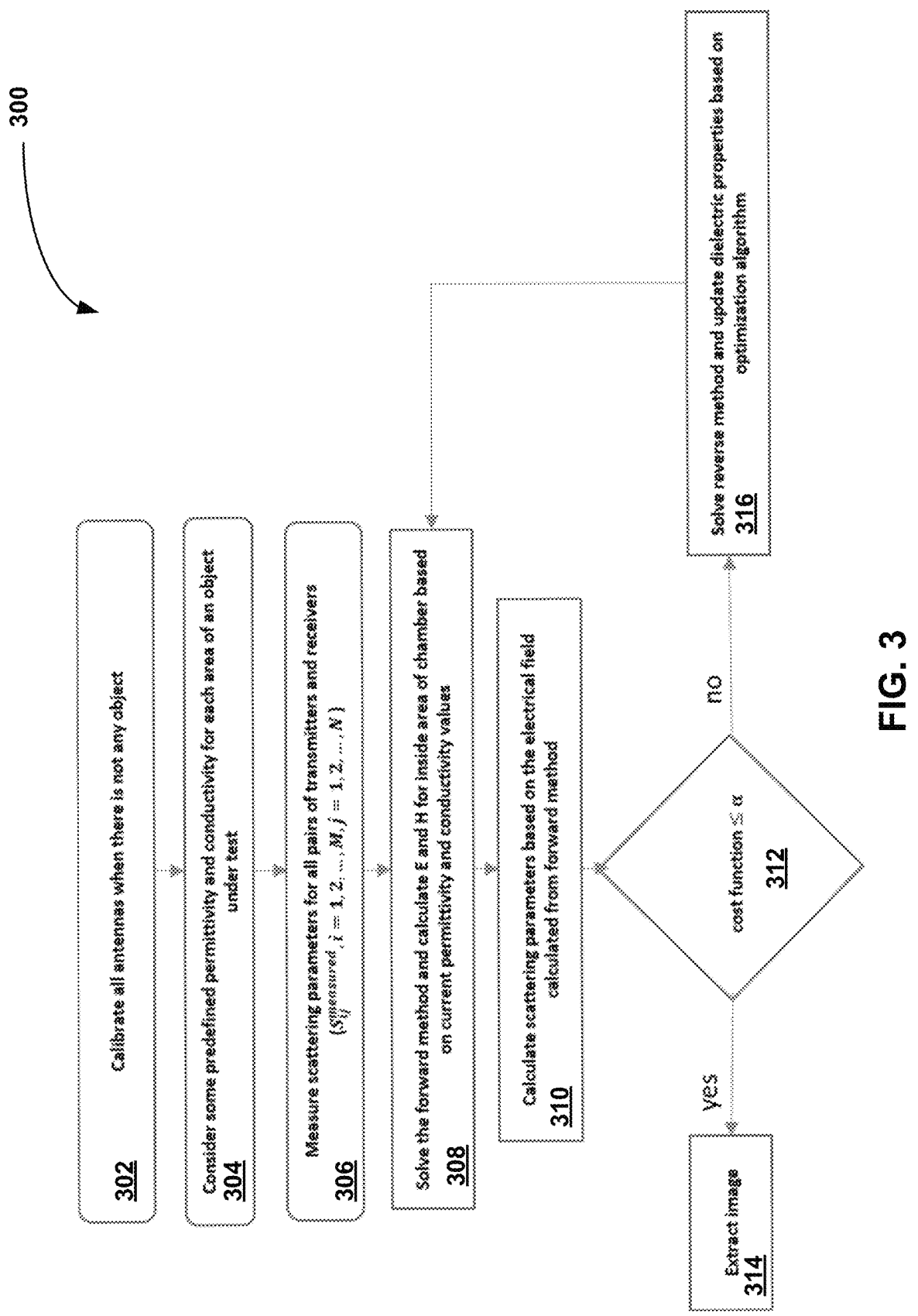

300

302 Calibrate all antennas when there is not any object

304 Consider some predefined permittivity and conductivity for each area of an object under test 306 Measure scattering parameters for all pairs of transmitters and receivers
$(S_{ij}^{measured}, i = 1, 2, ..., M, j = 1, 2, ..., N)$ 308 Solve the forward method and calculate E and H for inside area of chamber based on current permittivity and conductivity values 310 Calculate scattering parameters based on the electrical field calculated from forward method 312 cost function ≤ α no yes

314 Extract image

316 Solve reverse method and update dielectric properties based on optimization algorithm

Sensor part

412
Antenna array
2D/3D

Radio Frequency and Microwave circuit

414

Control

Control/data

416

Control and Monitoring

410

Data

Imaging part

420

Signal Processing
And
AI algorithms

422

Image display

424

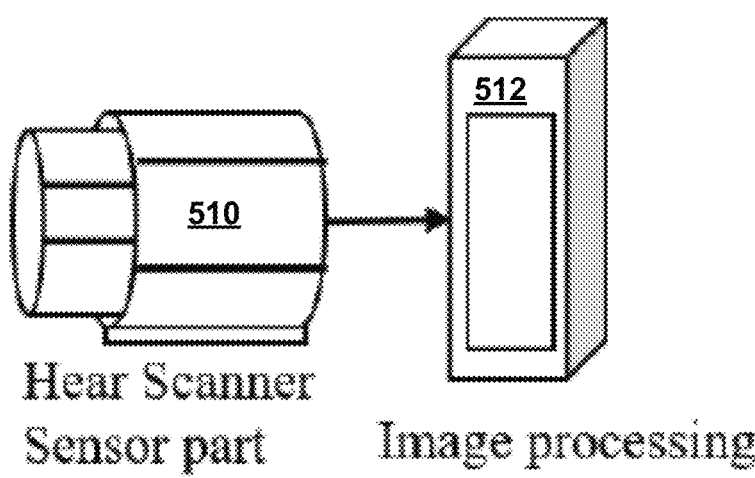
Hear Scanner
Sensor part     Image processing
FIG. 5A

Patch Antenna back side

Patch Antenna front side

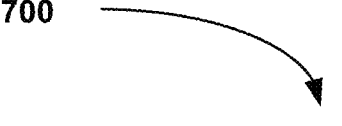
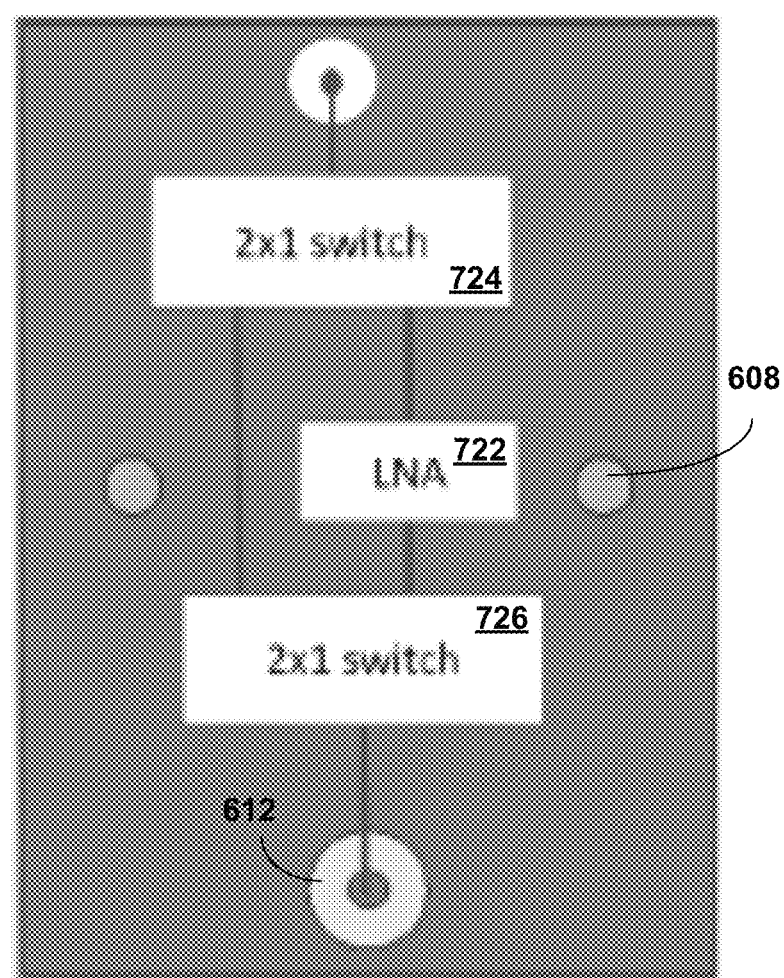
4-layer Patch Antenna including LNA and two 2x1 RF switches
FIG. 7

800
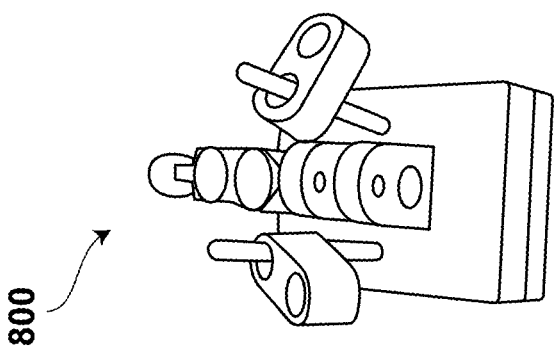
800
806
802b
802a
804
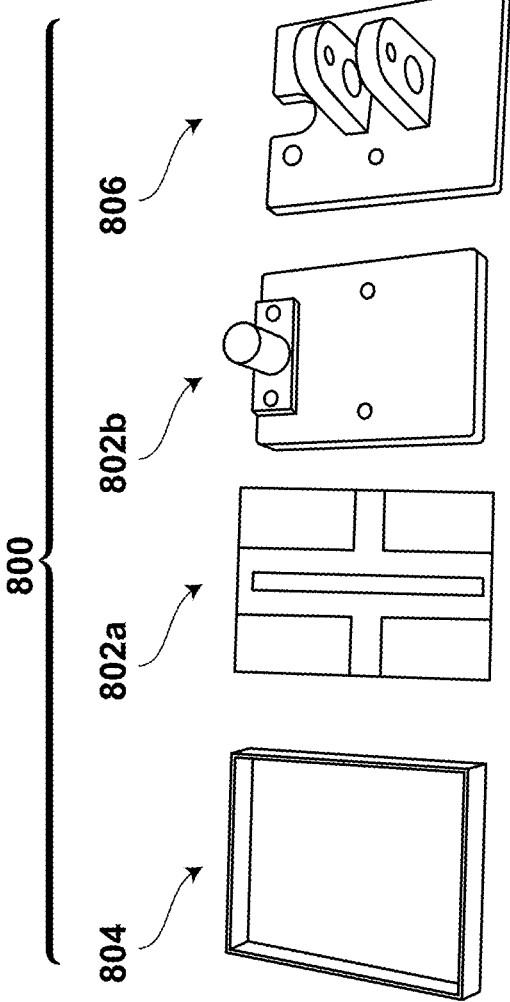
FIG. 8

900
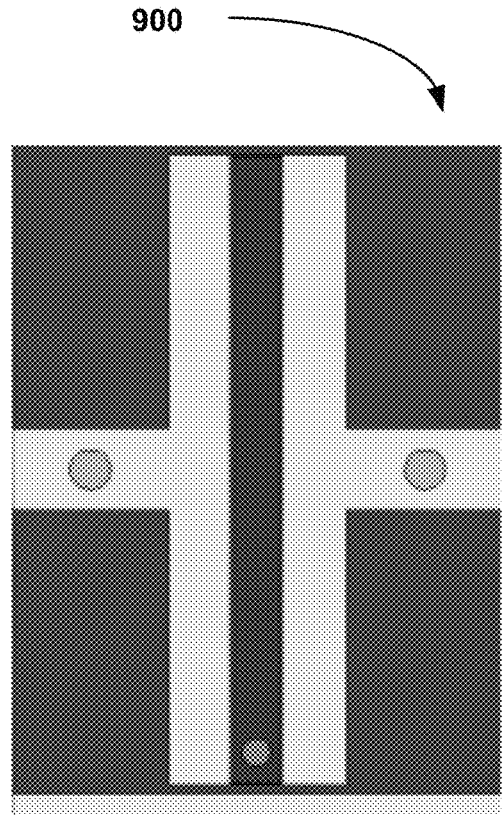
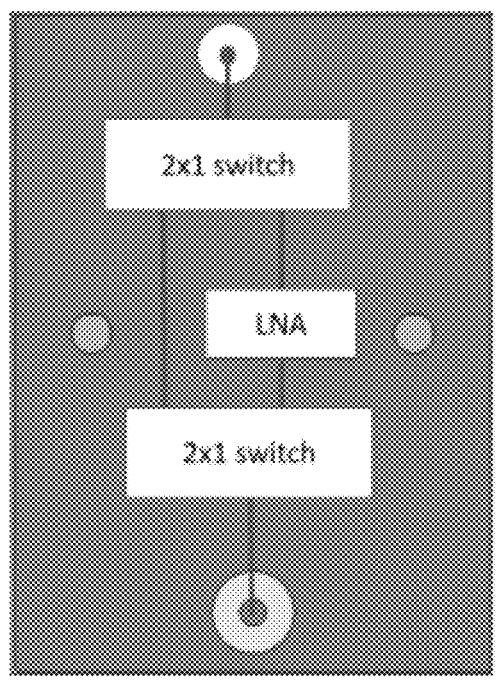
Front side             Back side
FIG. 9A
920
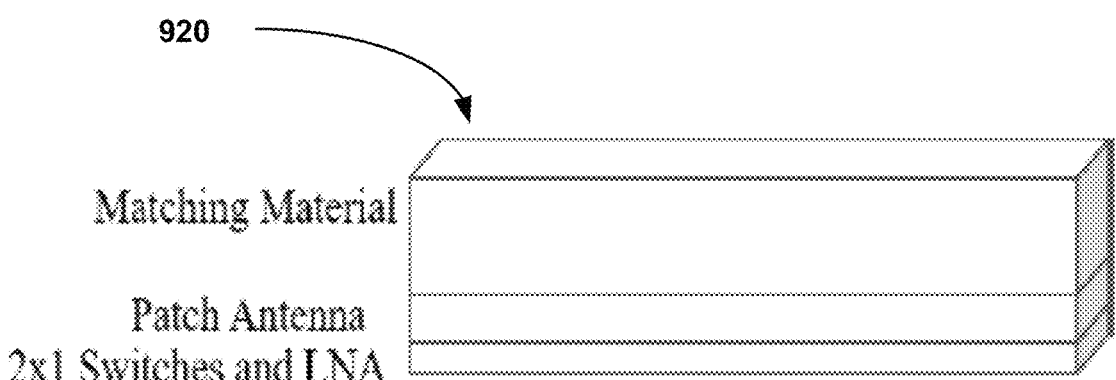
FIG. 9B

930

940

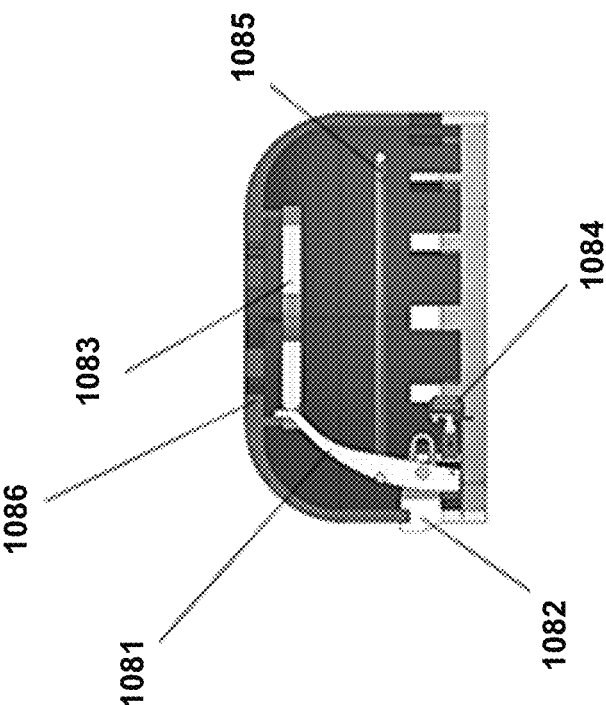
1085
1083
1086
1081
1084
1082
1080
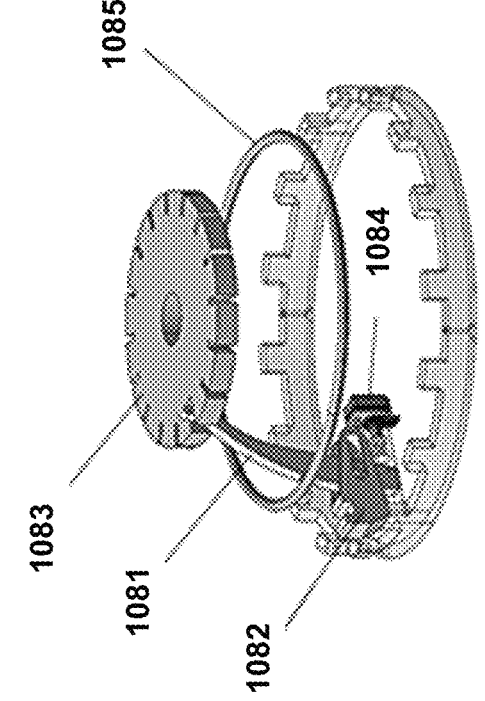
1085
1084
1083
1081
1082
FIG. 10D

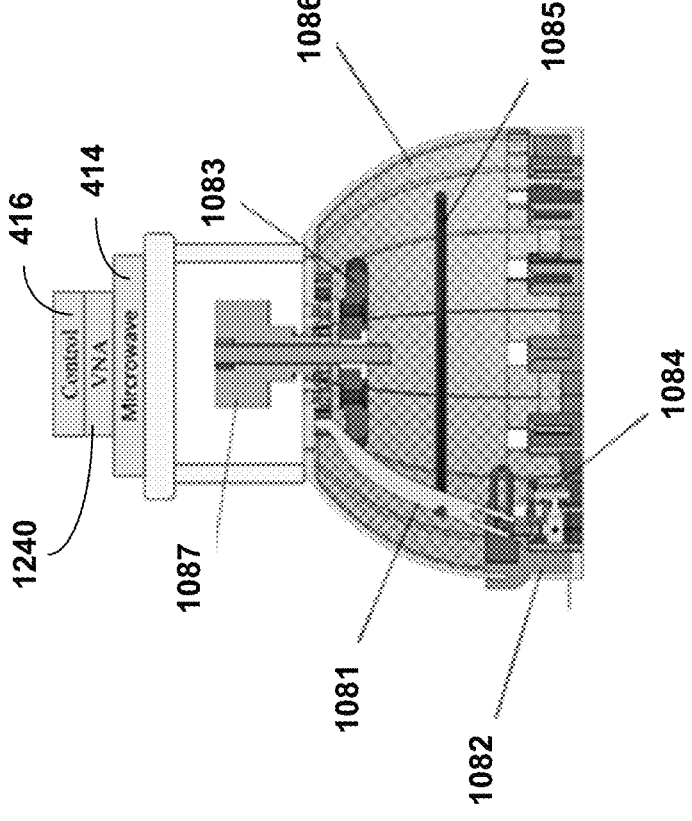
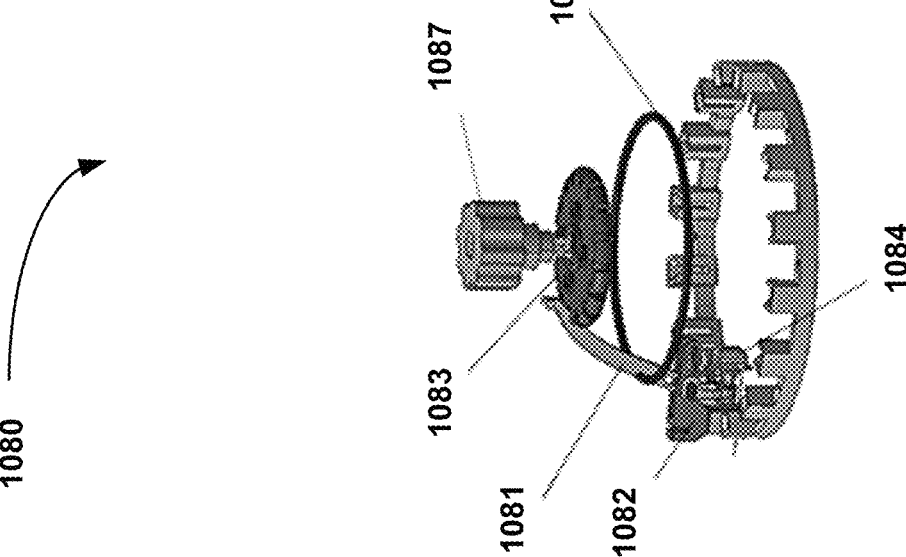
FIG. 10E

1100

1300

1350

APPARATUS, SYSTEM AND METHOD FOR ELECTROMAGNETIC IMAGING

CROSS-REFERENCE

This application is related to and claims priority to U.S. Application No. 63/195,119, entitled Apparatus, System And Method For Electromagnetic Imaging, and filed May 31, 2021.

FIELD

The present disclosure generally relates to electromagnetic imaging.

INTRODUCTION

When blood flow to a part of the brain is interrupted or diminished, brain tissue is deprived of oxygen and nutrients, resulting in a stroke. Within minutes, brain cells begin to die. Strokes are serious because they can cause long-term brain damage, physical impairment, and even death. The effects of a stroke on the brain can be permanent and irreversible. A stroke is a medical emergency that requires immediate treatment. Brain injury and other consequences can be avoided if intervention is taken early. Early stroke detection is one of the most successful preventative strategies for reducing long-term impairments, which has a huge economic impact worldwide.

About 85 percent of strokes are acute ischemic; they usually begin with a blood clot known as thrombus breaking to a small clot named embolus and move to the brain through the circulatory system. These clots block vessels and stop circulation of blood in some parts of the brain. The brain damage starts quickly. Thrombolytic is an efficient way to remove clot; however, stroke type should be recognized through clinical tests. Computed tomography (CT), magnetic resonance imaging (MRI), and positron emission tomography (PET) are reliable imaging methods for stroke detections. While these are standard imaging methods, these are costly solutions and thus, they are not affordable and widely accessible.

SUMMARY

In accordance with an aspect, there is provided an electromagnetic (EM) tomography head scanner comprising an antenna chamber, a radio frequency and microwave circuit, a control and monitoring unit, and a signal processing unit and an artificial intelligence unit.

In accordance with another aspect, there is provided a patch antenna designed with a wide microwave frequency range. It has an optimized cap (e.g., resin cap or any other type of cap) filled with proper matching material. This sensor has a flexible cover and easily fits the human head shape.

In accordance with another aspect, there is provided a mechanical structure having at least 4 arms and each arm has at least 4 antennas. This structure is adapted to a human head shape and can handle multiple antennas for a 2D or 3D imaging head scanner. In some embodiments, there may be approximately 50 antennas. In other embodiments, there may be fewer or more antennas.

In accordance with another aspect, there is provided an enhanced resolution using a stochastic optimization algorithm such as simulated annealing method.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

DESCRIPTION OF THE FIGURES

Embodiments will be described, by way of example only, with reference to the attached figures, wherein in the figures:

FIG. 3 illustrates, in a flowchart, an example of a method of EM tomography, in accordance with some embodiments;

FIGS. 5A and 5B illustrates other examples of EM tomography systems, in accordance with some embodiments;

FIG. 7 illustrates, in a block diagram, an example of a part of a microwave circuit, in accordance with some embodiments;

FIG. 8 illustrates components of a patch antenna assembly, in accordance with some embodiments;

FIGS. 9A and 9B illustrate another example of a patch antenna, in accordance with some embodiments;

FIG. 10D illustrates in different views an example of another mechanical structure for a brain scanner, in accordance with some embodiments;

FIG. 10E illustrates in different views the example of the mechanical structure for a brain scanner in more detail, in accordance with some embodiments;

It is understood that throughout the description and figures, like features are identified by like reference numerals.

DETAILED DESCRIPTION

Figure 1A:
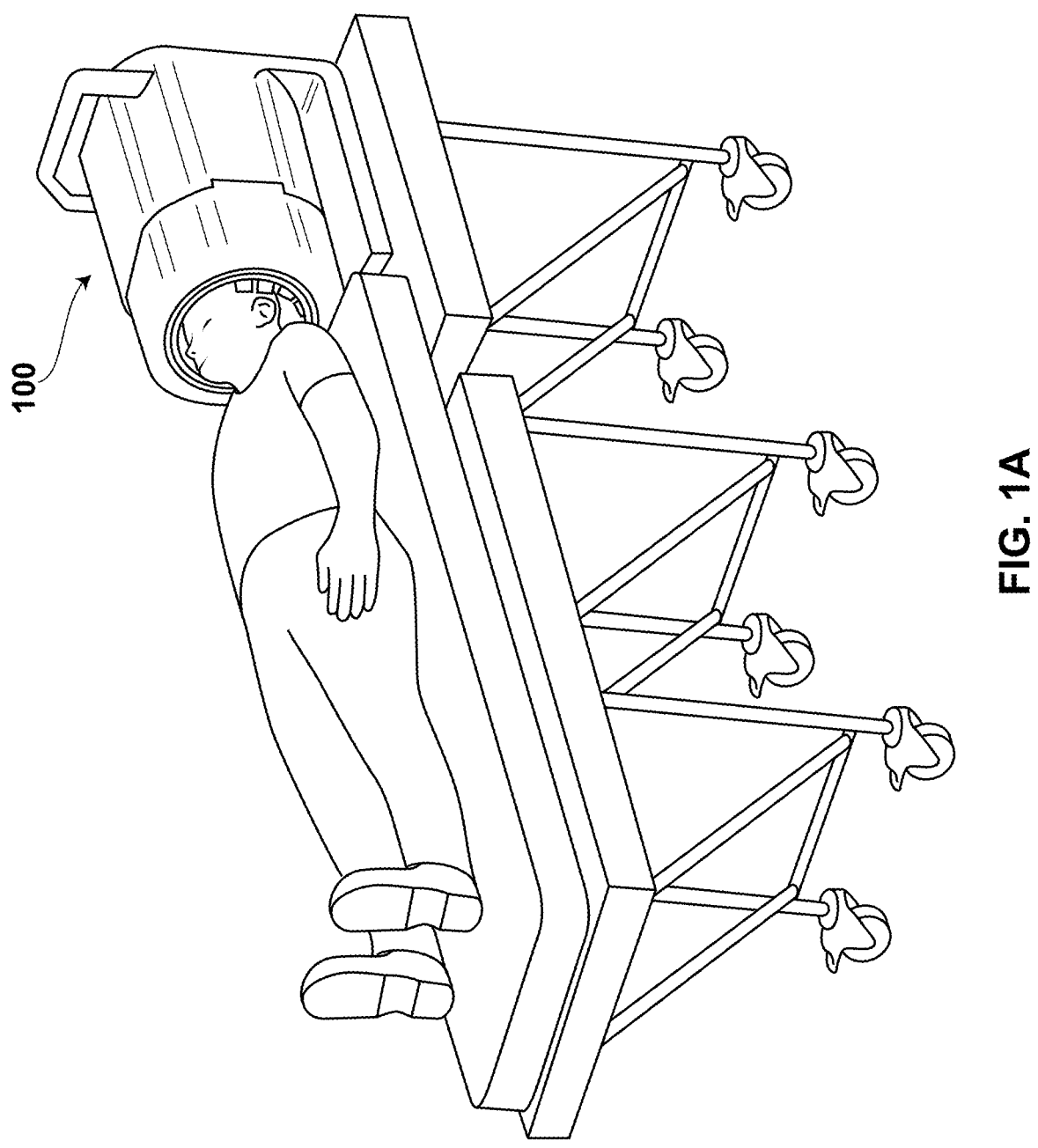
FIGS. 1A and 1B illustrate example of EM head scanner systems, in accordance with some embodiments.

Embodiments of methods, systems, and apparatus are described through reference to the drawings. Applicant notes that the described embodiments and examples are illustrative and non-limiting. Practical implementation of the features may incorporate a combination of some or all of the aspects, and features described herein should not be taken as indications of future or existing product plans.

An electromagnetic tomographic imaging system includes a plurality of antennas, a microwave circuit, and a forward algorithm (e.g., a Finite Difference Time Domain (FDTD) algorithm or other algorithm) and a inverse algorithm (e.g., a simulated annealing inverse algorithm or another algorithm). Scattering parameters are gathered with high Signal to Noise Ratio (SNR) and low antenna coupling. In some embodiments, the scattering parameters may be gathered in frequency and space. This structure is adapted to human head shape and can handle multiple antennas with spatial arrangement around the human head for a 2D or 3D image scanning. In some embodiments, there may be approximately 50 antennas. In other embodiments, there may be fewer or more antennas. An optimization algorithm (e.g., a simulated annealing algorithm or other optimization algorithm) solves electromagnetic inverse problem to achieve a global optimum solution with a reasonable time and proper image resolution.

In some embodiments, there is provided a new patch antenna designed with a wide microwave frequency range. It has an optimized cap (e.g., a resin cap or other type of cap) filled with proper matching material. This sensor has a flexible cover and easily fits the human head shape.

In some embodiments, a mechanical structure has at least 4 arms and each arm has at least 4 antennas. This structure is adapted to a human head shape and as noted above can handle multiple antennas for 2D or 3D imaging head scanner.

In some embodiments, an enhanced resolution using an optimization method (e.g., a simulated annealing (SA) method or other optimization method) is provided. The ill-posed nature of the electromagnetic tomography restricted exact optimization algorithms such as gradient descent. Also, these algorithms are very slow and can get stuck in local optimums. A stochastic inverse algorithm is the best option to achieve a global optimum solution with a reasonable time and proper image resolution.

Electromagnetic imaging is a promising solution for emergency and on-site brain imaging. Generally, there are two electromagnetic imaging methods, radar-based and tomography imaging. The radar-based methods are used in homogeneous environments; on the other hand, electromagnetic tomography (EM) methods are applied for heterogeneous conditions. EM tomography is a non-invasive method and works based on tissue dielectric properties. Any anomaly and disease in human biological tissues that has different dielectric properties can be detected by EM tomography. These detections include but not limited to breast cancer, brain injuries, and broken bone. The most important specific applications of this technology for the brain are stroke and tumor detection and tracking. The human brain has multilayer biological tissues including skin, bone, gray matter, white matter, and cerebral Spinal Fluid (CSF). These layers have different dielectric properties and any anomaly in each layer can be extracted by EM tomography.

Figure 1B:
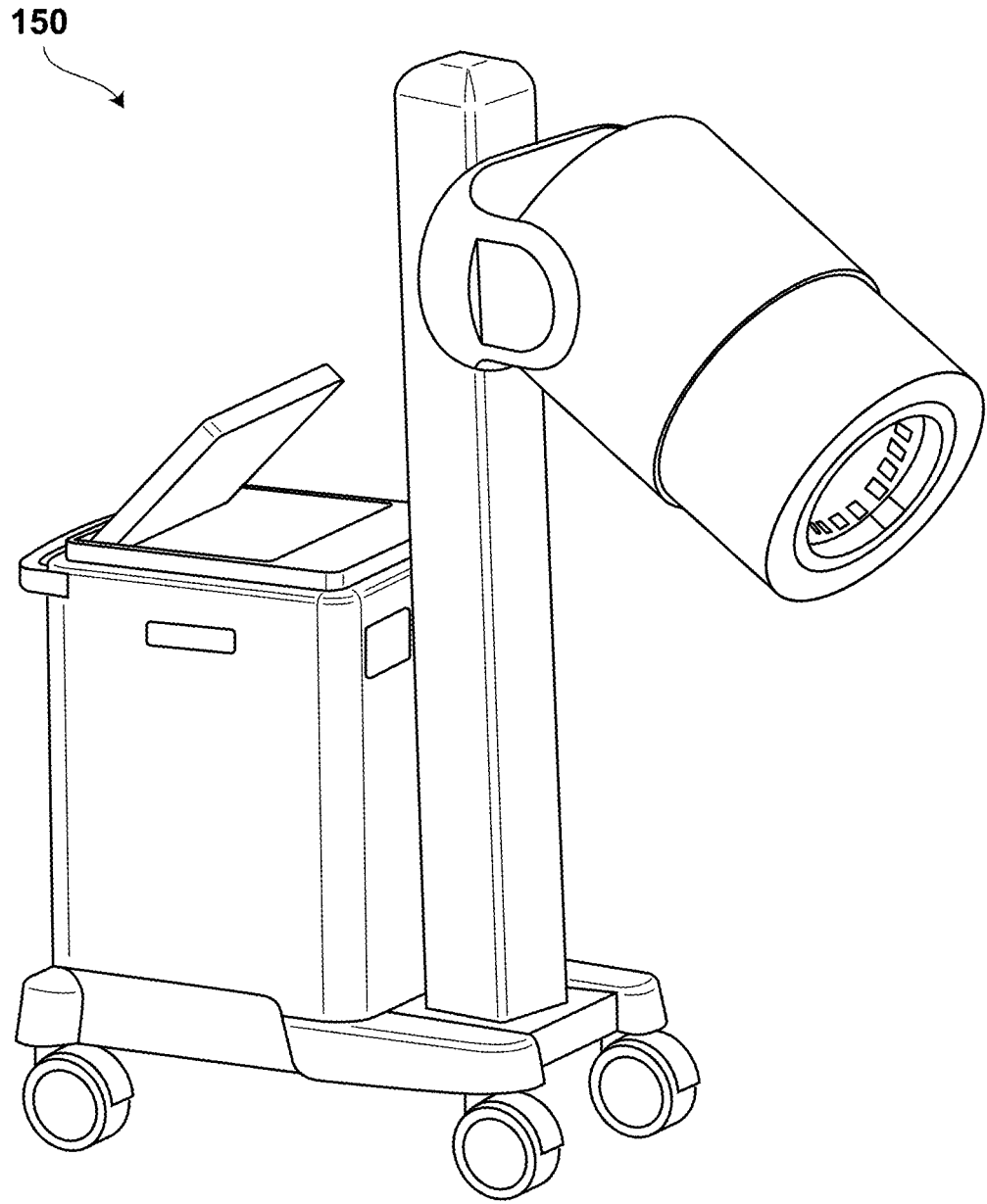

In some embodiments, EM head scanners may be compact and portable systems. FIGS. 1A and 1B illustrate examples of EM head scanner systems 100, 150, in accordance with some embodiments. The primary application is for early detection of stroke and can be used for emergency rooms, ambulances and even physicians' offices. This system should be very user friendly that needs minimum preparation and installation for nurses and emergency doctors. At a more advanced level, the applications of the brain scanner may be extended to detection and tracking of Alzheimer and Parkinson diseases.

Figure 2:
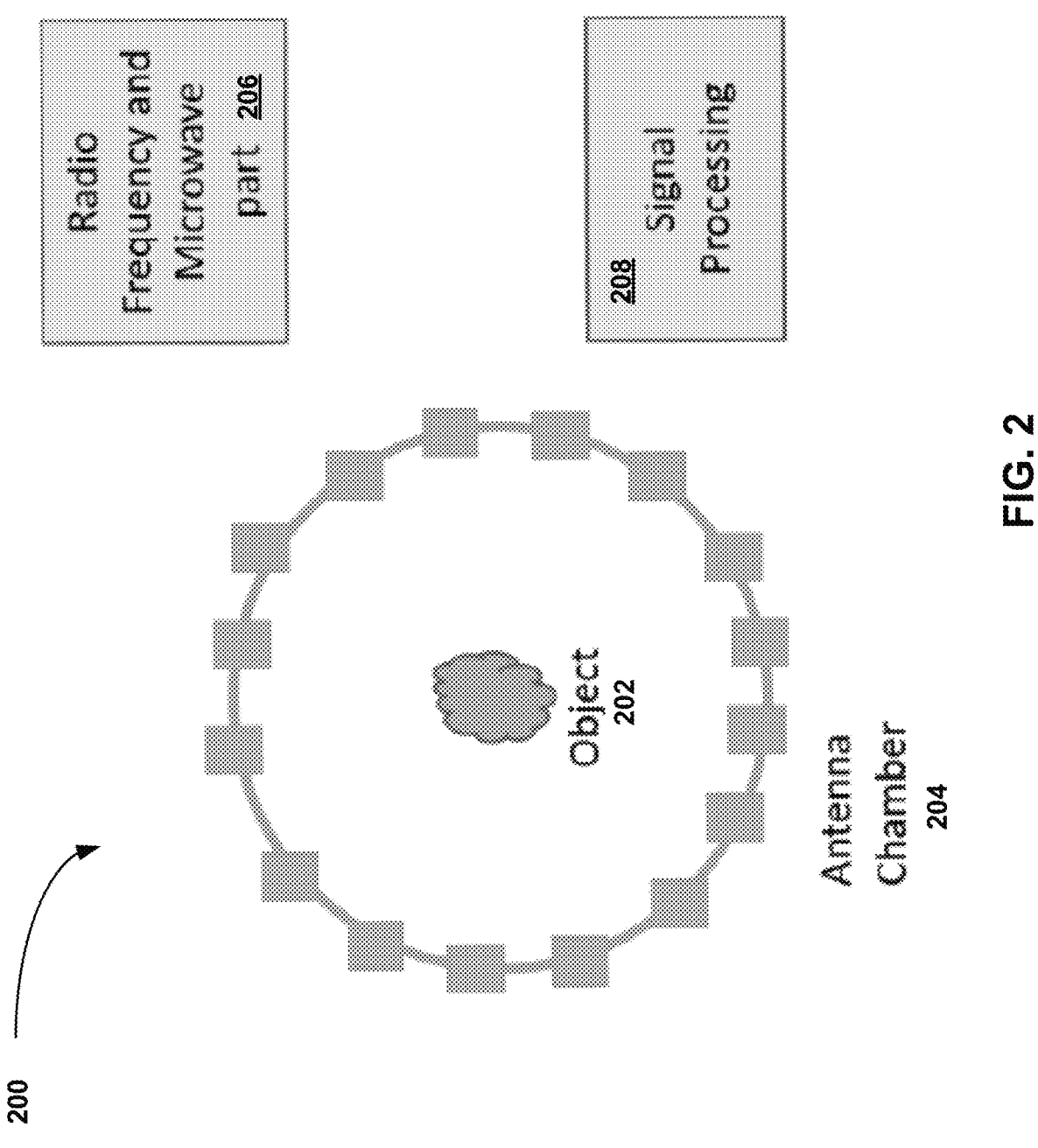
FIG. 2 illustrates, in a schematic, an example of an EM tomography system, in accordance with some embodiments.

Generally, in electromagnetic tomography an object 202 with unknown dielectric properties is put in a chamber 204 surrounded with multiple antennas around it. FIG. 2 illustrates, in a schematic, an example of an EM tomography system 200, in accordance with some embodiments. The system 200 includes a Radio Frequency and Microwave unit 206 and a signal processing unit 208. The antennas may be put in 2-dimensional or 3-dimensional arrangements. In each scenario one or multiple antennas are transmitting electromagnetic signals and others are receiving them. The electromagnetic fields are sampled at both receiver and transmitter sides in time domain or frequency domain. Then, the scattering parameters, for some or all combinations of transmitters and receivers are calculated. These measured scattering parameters are applied to EM tomography algorithms to reconstruct the brain images. FIG. 3 illustrates, in a flowchart, an example of a method of EM tomography 300, in accordance with some embodiments. This method 300 is implemented with an iterative algorithm including forward and inverse solutions. There is a cost function which should be less than some specific threshold after its convergence.

The method 300 includes calibrating 302 all antennas when there is no object present. Next, some predefined permittivity and conductivity are considered 304 for each area of an object under test. Next, scattering parameters (e.g., reflection and transmission parameters) may be measured 306 for all pairs of transmitters and receivers. This can be denoted as: $S_{ij}^{measured}$, i=1, 2, . . . , M; j=1, 2, . . . , N). Next, the forward method is solved and electric field intensity (E) and magnetic field intensity (H) are determined 308 for the inside area of the chamber 204 based on current permittivity and conductivity values. The E may be measured in volts per ampere (V/A) and the H may be measured in amperes per meter (A/m). Next, the scattering parameters are determined 310 based on the electrical field calculated from the forward method. If the cost function is less than or equal to a threshold value a 312, then an image is extracted 314. Otherwise 312, a reverse method is determined and dielectric properties are updated 316 based on the optimization algorithm. Other steps may be added to the method 300. The method 300 will be described in more detail below.

Figure 4:
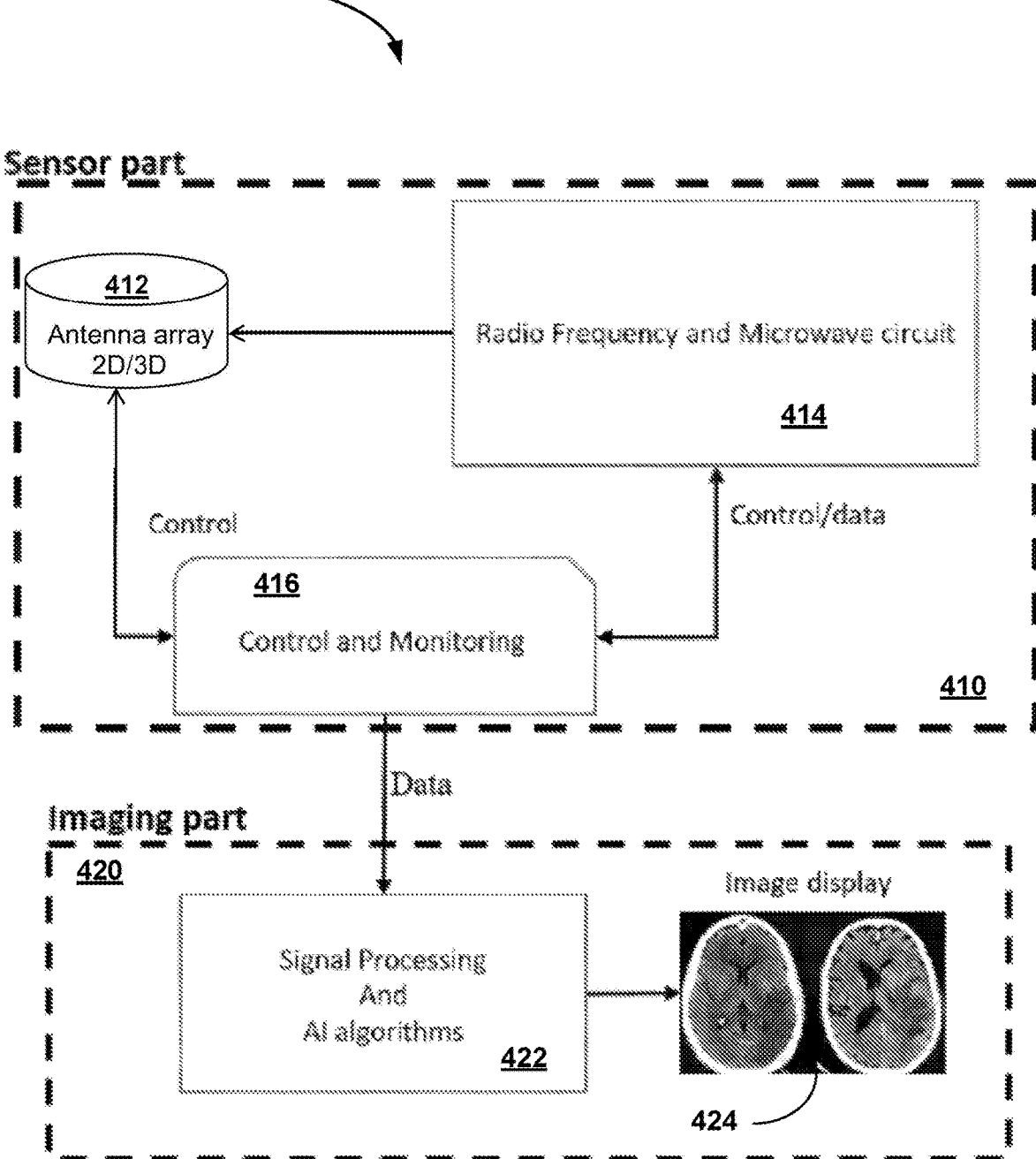
FIG. 4 illustrates, in block diagram, an example of an EM tomography head scanner, in accordance with some embodiments.

FIG. 4 illustrates, in block diagram, an example of an EM tomography head scanner 400, in accordance with some embodiments. This example includes four sections, including 1) an antenna chamber or array 412, 2) a Radio Frequency (RF) and microwave circuit 414, 3) a controller 416, and 4) a signal processing and Artificial Intelligence (AI) 412. Data is collected by the sensor unit 410 and processed by the imaging unit 420 in order to provide an image display 424.

Figure 5B:
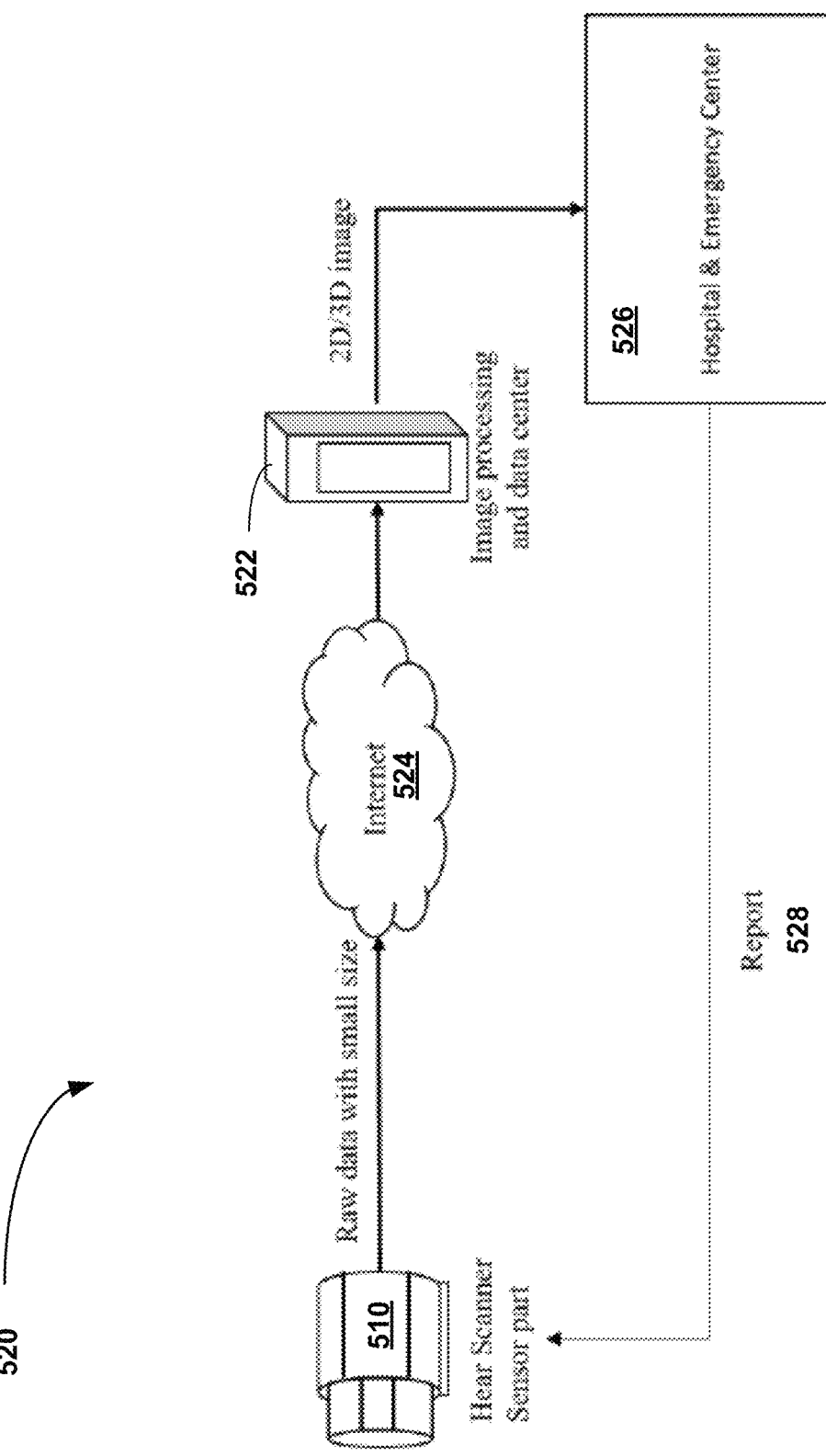

FIGS. 5A and 5B illustrates other examples of EM tomography systems 500, 520, in accordance with some embodiments. The imaging part 512 can be separated from the sensor part 510; in other words, image processing can be done in one unit 512 as shown in FIG. 5A, or in a remote server 522 via a network connection 524 as shown in FIG. 5B. The 2D/3D image may then be sent to a medical center 526 for processing and a report and decision 528 is sent to the patient location (e.g., via communication connection).

Figure 5C:
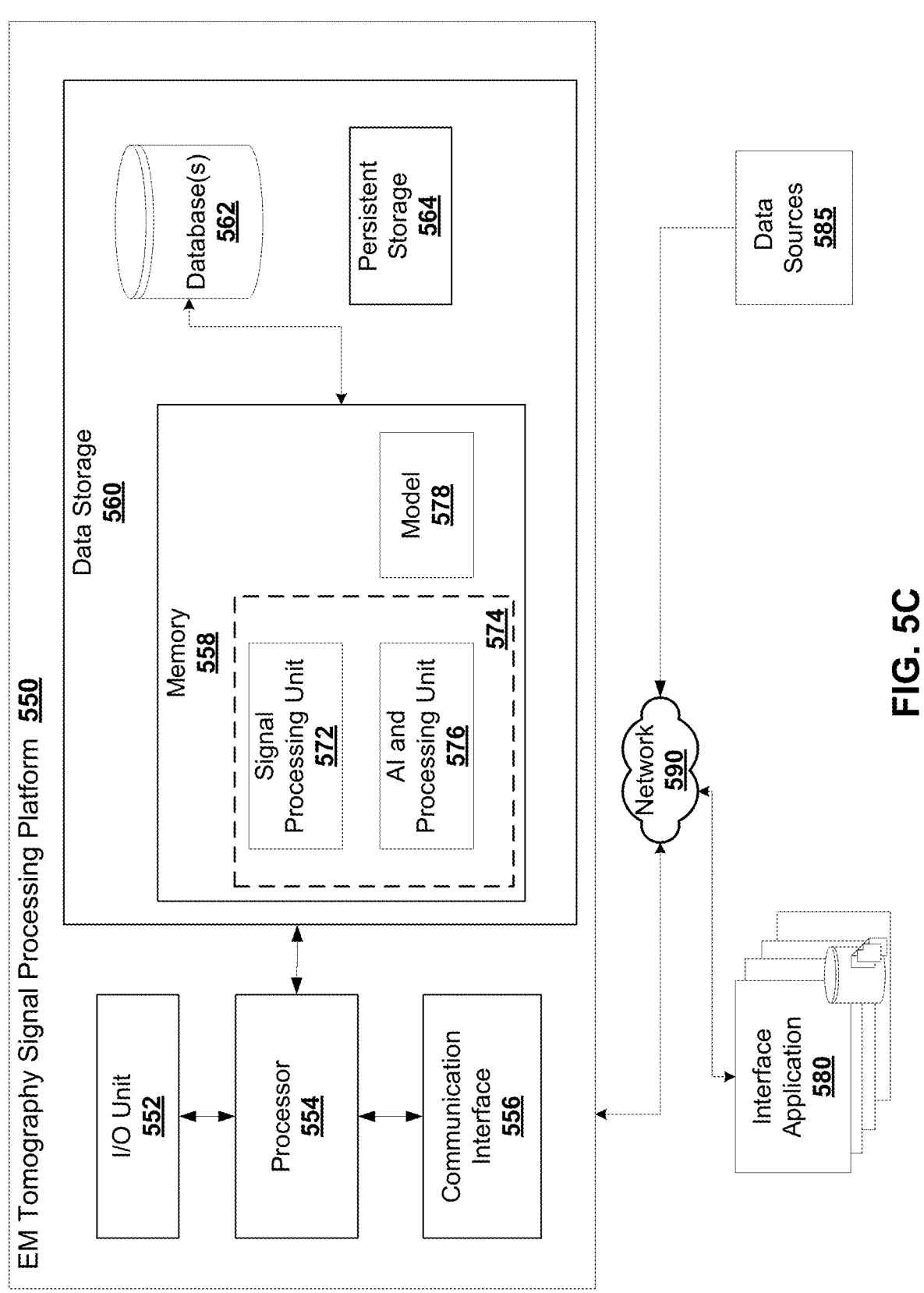
FIG. 5C illustrates, in a schematic, an example of an EM tomography signal processing platform, in accordance with some embodiments.

FIG. 5C illustrates, in a schematic, an example of an EM tomography signal processing platform 550, in accordance with some embodiments. The platform 550 may be an electronic device connected to interface application 580 and data sources 585 via network 590. The platform 550 can implement aspects of the processes described herein.

The platform 550 may include a processor 554 and a memory 558 storing machine executable instructions to configure the processor 554 to receive a voice and/or text files (e.g., from I/O unit 552 or from data sources 585). The platform 550 can include an I/O Unit 552, communication interface 556, and data storage 560. The processor 554 can execute instructions in memory 558 to implement aspects of processes described herein.

The platform 550 may be implemented on an electronic device and can include an I/O unit 552, a processor 554, a communication interface 556, and a data storage 560. The platform 550 can connect with one or more interface applications 580 or data sources 585. This connection may be over a network 590 (or multiple networks). The platform 550 may receive and transmit data from one or more of these via I/O unit 552. When data is received, I/O unit 552 transmits the data to processor 554.

The I/O unit 552 can enable the platform 550 to interconnect with one or more input devices, such as a keyboard, mouse, camera, touch screen and a microphone, and/or with one or more output devices such as a display screen and a speaker.

The processor 554 can be, for example, any type of general-purpose microprocessor or microcontroller, a digital signal processing (DSP) processor, an integrated circuit, a field programmable gate array (FPGA), a reconfigurable processor, or any combination thereof. The processor 554 can be a parallel processing platform including multiple Central Processing Units (CPUs) and/or multiple Graphics Processing Units (GPUs).

The data storage 560 can include memory 558, database(s) 562 and persistent storage 564. Memory 558 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Data storage devices 560 can include memory 558, databases 562 (e.g., graph database), and persistent storage 564.

The communication interface 556 can enable the platform 550 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., Wi-Fi, WiMAX, 5G), SS7 signaling network, fixed line, local area network, wide area network, and others, including any combination of these.

The platform 550 can be operable to register and authenticate users (using a login, unique identifier, and password for example) prior to providing access to applications, a local network, network resources, other networks and network security devices. The platform 550 can connect to different machines or entities.

The data storage 560 may be configured to store information associated with or created by the platform 550. Storage 560 and/or persistent storage 564 may be provided using various types of storage technologies, such as solid state drives, hard disk drives, flash memory, and may be stored in various formats, such as relational databases, non-relational databases, flat files, spreadsheets, extended markup files, etc.

The memory 558 may include a model 578, and a processing unit 574 that includes a signal processing unit 572 and an AI and processing unit 576.

Figure 6B:
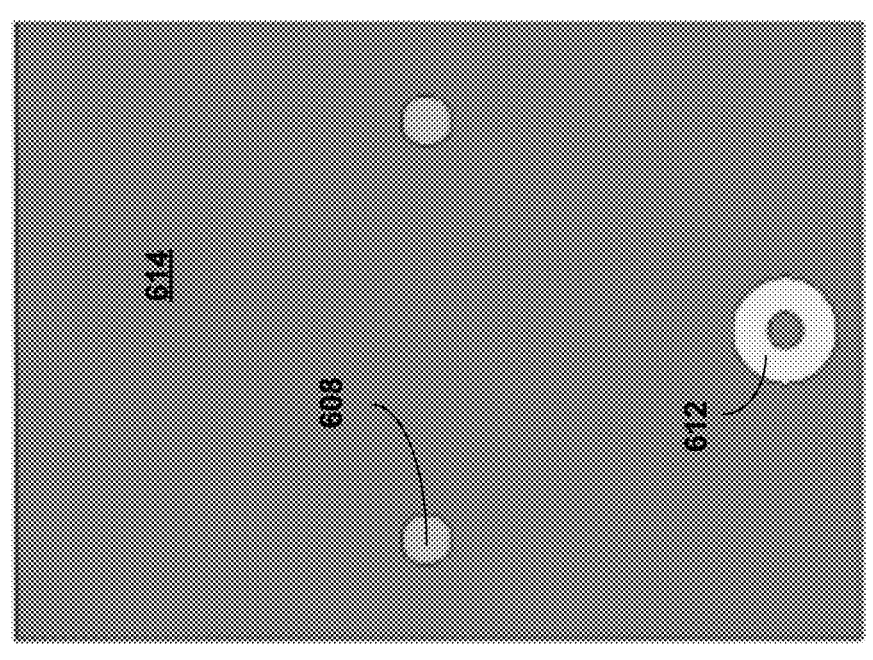
FIGS. 6A and 6B illustrate an example of a compact patch antenna, in accordance with some embodiments.
Figure 6A:
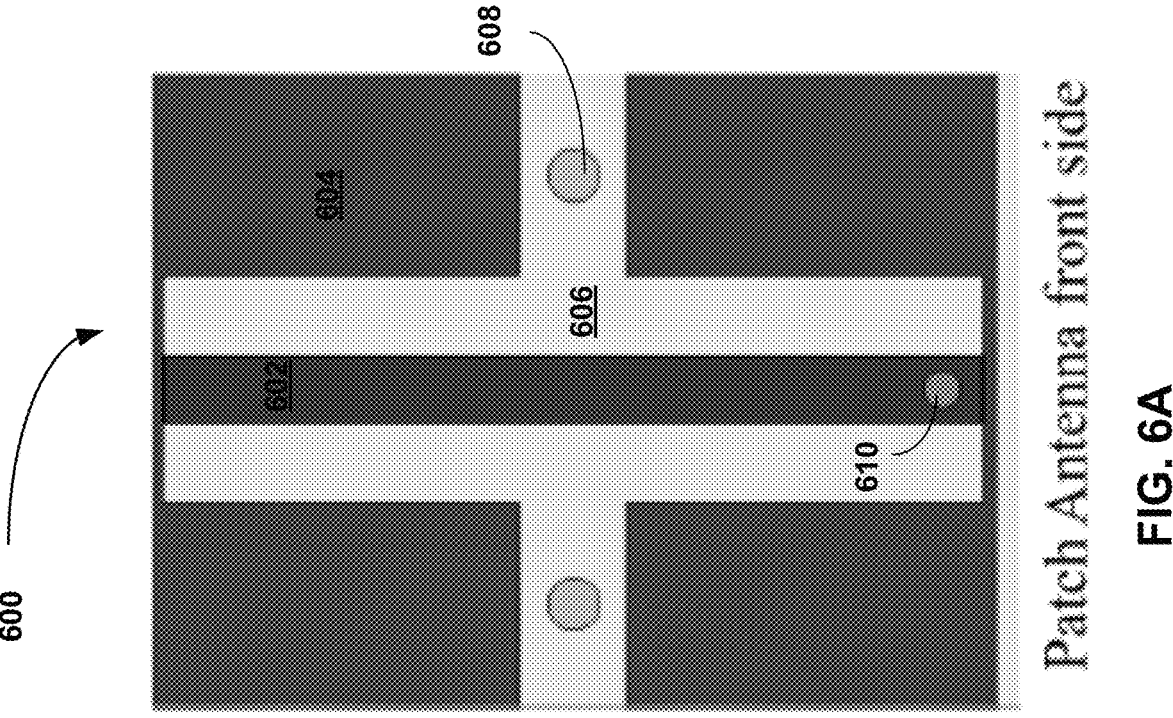

There are different type of antennas using for human brain imaging. A compact, high gain antenna with wide frequency band is the best antenna. FIGS. 6A and 6B illustrate an example of a compact patch antenna 600, in accordance with some embodiments. This antenna 600 is a two-layer Printed Circuit Board (PCB) and as shown in FIGS. 6A and 6B, one side (e.g., front side shown in FIG. 6A) has multiple patches 602, 604 for radiating electromagnetic signal and the other (e.g., back side shown in FIG. 6B) is a ground side 614. The patches 602, 604 are placed over a substrate 606 and holes 608 for insertion of plastic tubes for injection of matching material. Radio Frequency (RF) connector 612 may be connected to patch 602 using via 610. Some parts of microwave circuit including a Low Noise Amplifier (LNA) and two Radio Frequency (RF) switches can be added to this antenna when antenna has at least four layers. This part of microwave and RF circuit can be printed in separate PCB and connected to the antenna board. FIG. 7 illustrates, in a block diagram, an example of a part of a microwave circuit 700, in accordance with some embodiments. FIG. 7 shows a four layer patch antenna including LNA 722 and two 2×1 RF switches 724, 726. FIG. 8 illustrates components of a patch antenna assembly 800, in accordance with some embodiments. Each integrated sensor has a patch antenna 802a, 802b, a matching material cap 804 and a holder 806 as shown in FIG. 8. The integrated sensor 800 may also have two silicon tubes that are using for injecting matching material into the cap if it is liquid or gel and the antenna is immersed in the matching material.

Figure 9C:
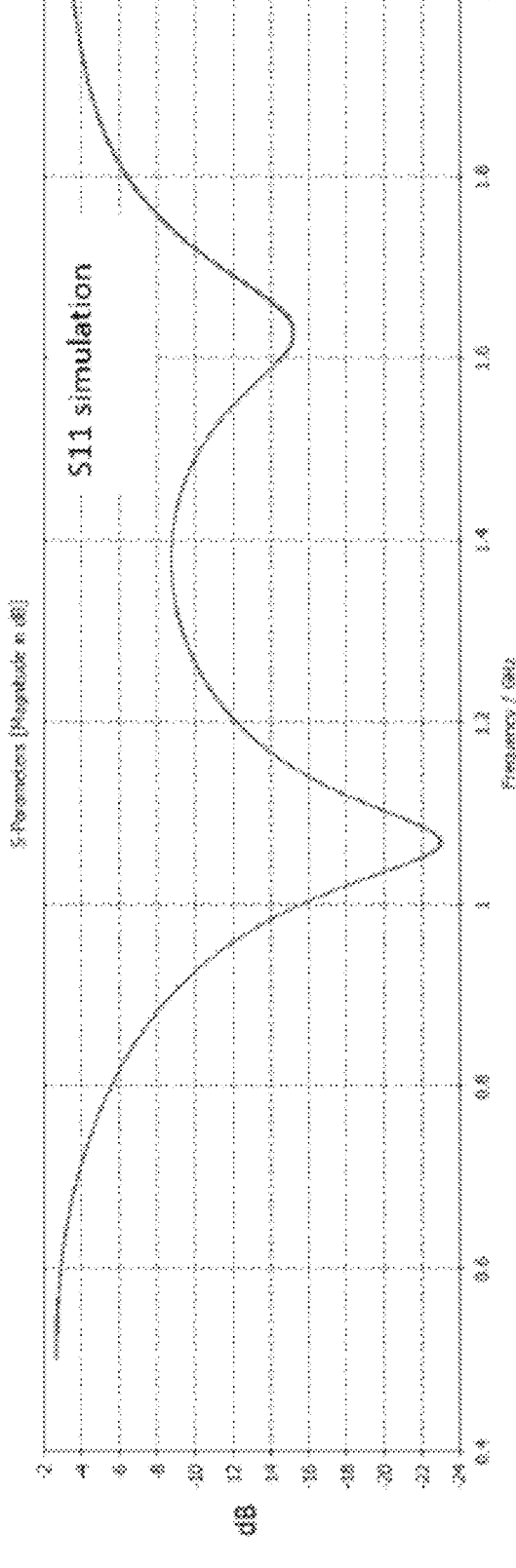
FIGS. 9C and 9D show an example of the reflection response of the antenna, in accordance with some embodiments.
Figure 9D:
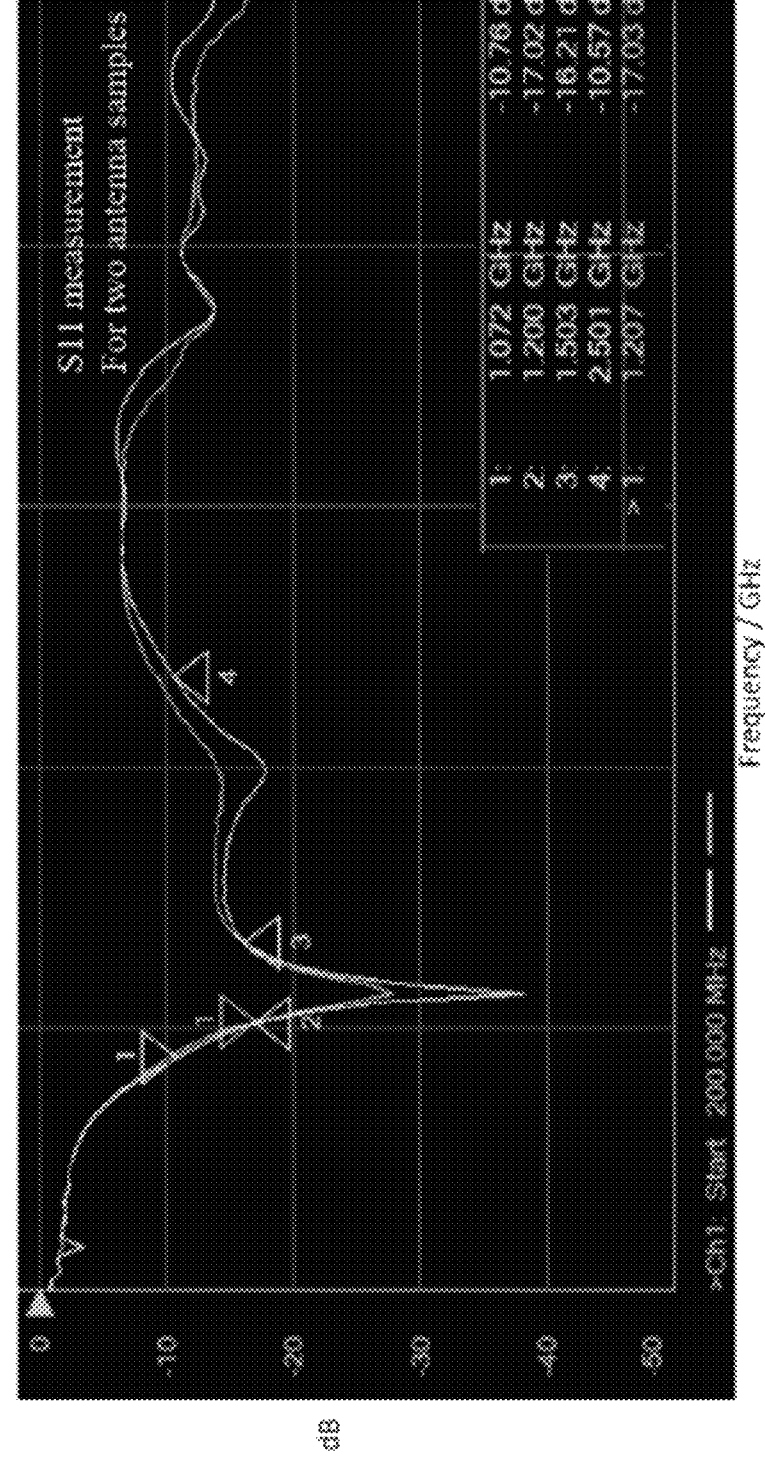

For some designs all antennas must be inside a lossy matching material which is liquid or gel. Usually, antennas are fixed in a circular or a hemisphere structure with considerable distance from the human brain. This configuration improves scattering parameters and decreases antenna dimensions. On the other hand, Signal to Noise Ratio (SNR) deteriorates because of the considerable distance of the antenna from the imaging object and high lossy matching material. Moreover, this structure of matching material can increase antenna coupling which decreases SNR more. If there is not any matching material, antenna dimensions increase, and the scattering parameters are sensitive to the position of the human head. In some designs, a flexible layer which is not liquid or gel is put in front of the antenna. This scenario does not give enough dielectric properties and has low return loss. Furthermore, this design cannot be fit with the shape of the imaging object. The antenna type can be waveguide, patch, slot, and dipole antennas. A perfect design has compact antennas with small dimensions and very low reflection and high power radiation, low interference and coupling from other antennas, and should work in a wide frequency range. In some embodiments, the antenna design is a specific patch antenna including a layer of liquid or gel matching material on the patch antenna. FIGS. 9A and 9B illustrate another example of a patch antenna 900, 920, in accordance with some embodiments. This compact patch antenna has a wide frequency range with an optimised matching material held by a flexible cap. This matching material has average dielectric properties of the human head and a thickness between approximately 2 mm to approximately 10 mm. FIGS. 9C and 9D show an example of the reflection response of the antenna 930, 940, in accordance with some embodiments. This antenna has low loss and small coupling with other antennas. The working frequency is between 1 GHz to 2 GHz. The EM tomography is implemented for one or multiple frequencies in this frequency range. FIG. 9D shows that the measurement is similar to the simulation shown in FIG. 9C.

Figure 10A:
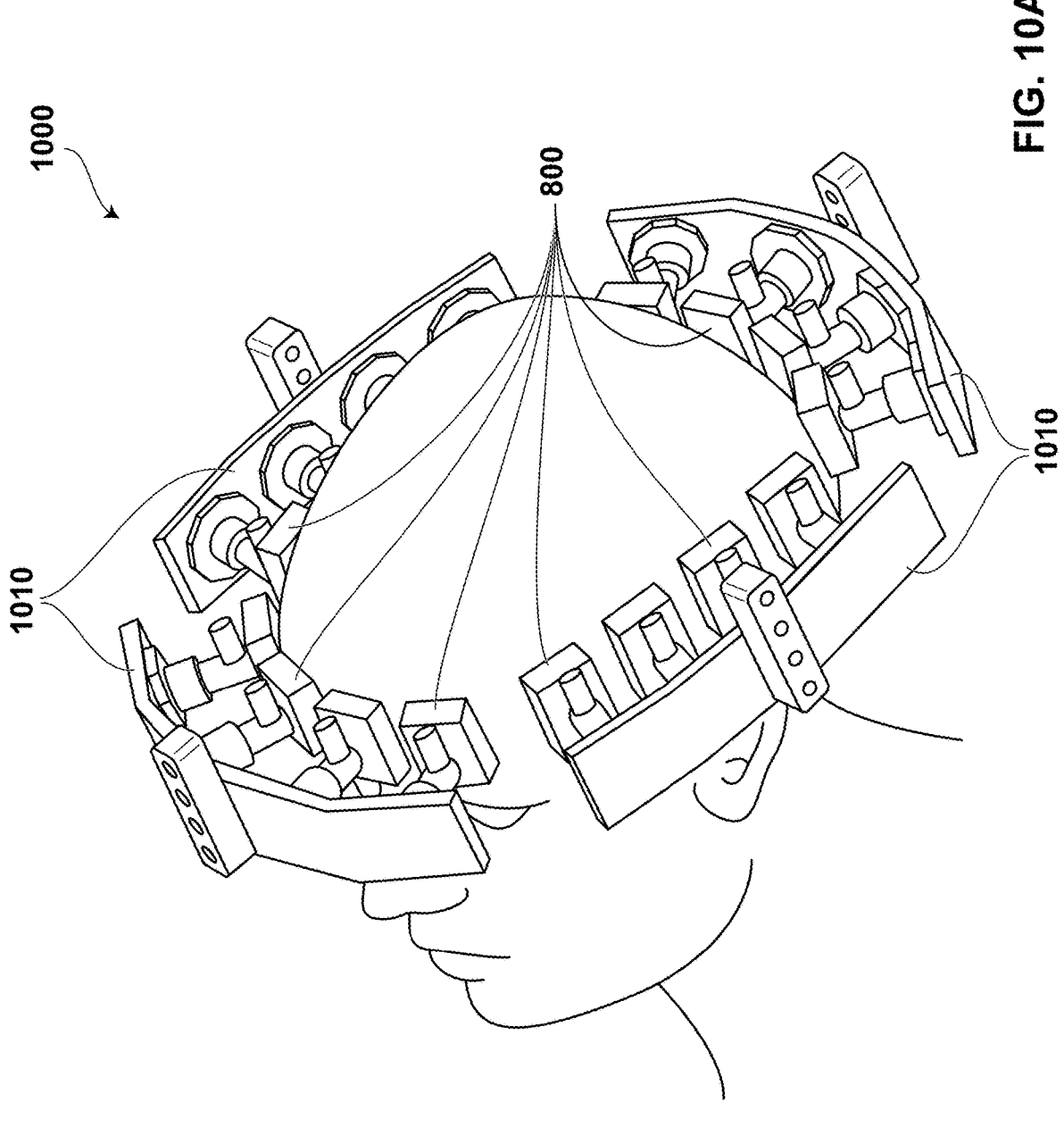
FIG. 10A illustrates an example of an antenna structure, in accordance with some embodiments.
Figure 10B:
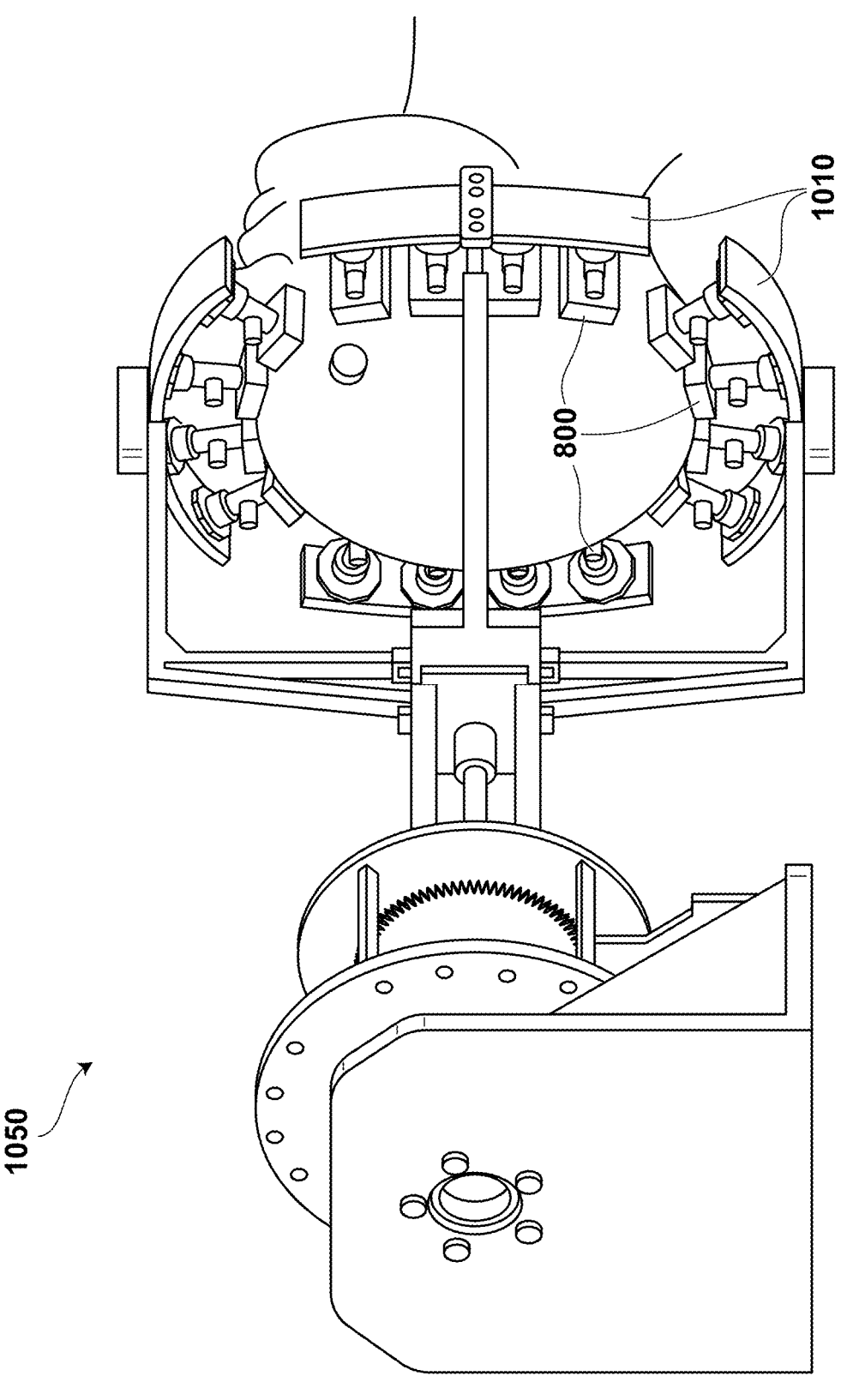
FIG. 10B illustrates another example of an EM tomography system, in accordance with some embodiments.
Figure 10C:
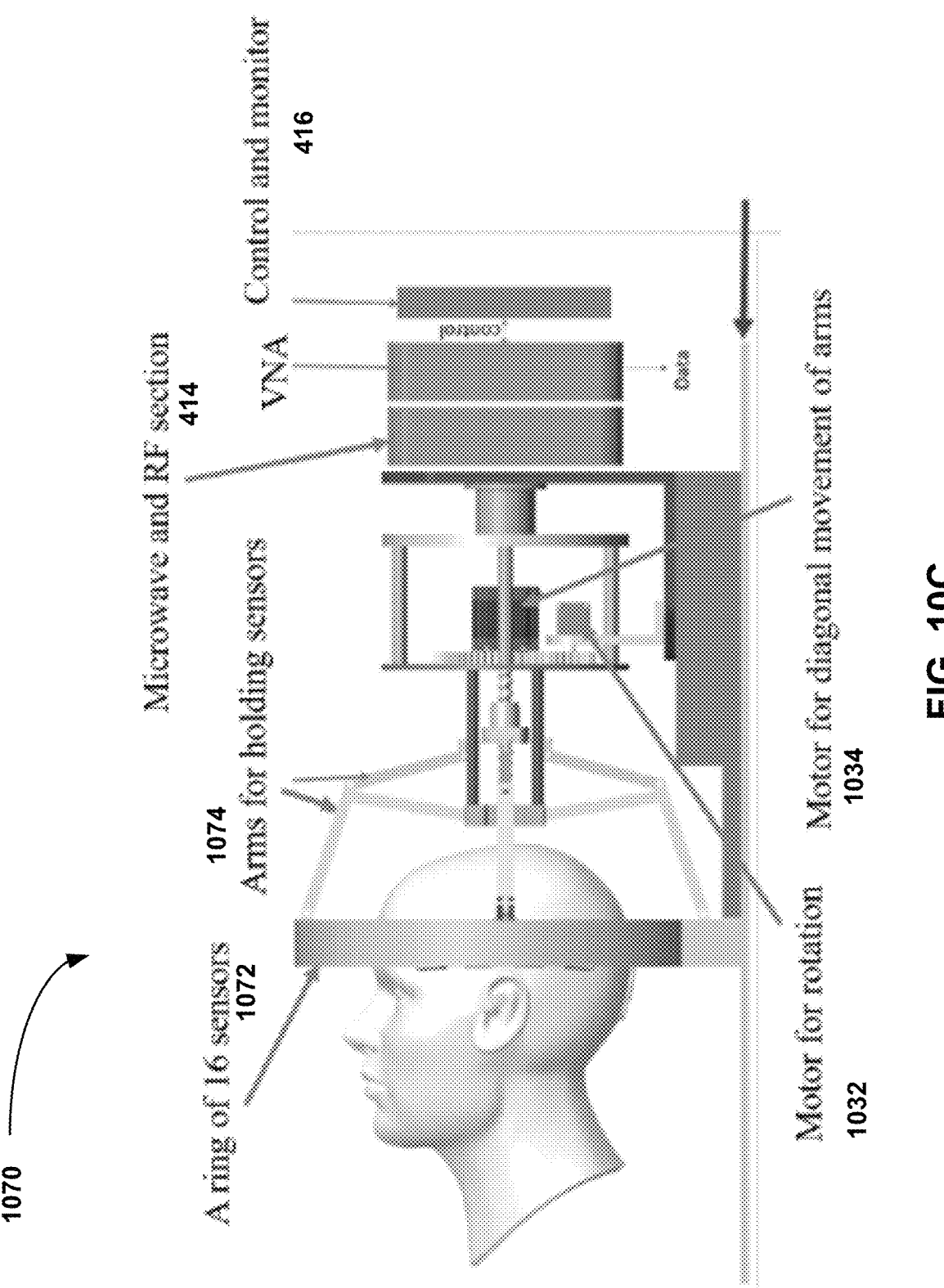
FIG. 10C illustrates another example of an EM tomography system, in accordance with some embodiments.

FIG. 10A illustrates an example of an antenna structure 1000, in accordance with some embodiments. FIG. 10B illustrates another example of an EM tomography system 1050, in accordance with some embodiments. In some embodiments, the 2-dimensional imaging scanner has 16 integrated sensors 800. There are 4 arms 1010 and each arm has 4 sensors 800 as shown in FIG. 10A and FIG. 10B. FIG. 10C illustrates another example of an EM tomography system 1070, in accordance with some embodiments. There are two motors 1032, 1034 which control the diagonal and rotational movements as shown in FIG. 10C.

In some embodiments, the antenna may be a four layer Printed Circuit Board (PCB) including antenna patch 802a, 802b and two 2×1 switches 724, 726 and one Low Noise Amplifier (LNA) 722. In some embodiments, additional lawyers may be added to the PCB, including an additional ground layer and a microwave circuit layer. In some embodiments, there is an array 1072 of 16 antennas in 2D format as shown in FIG. 10A. Arms 1072 for holding the sensors 800 are also shown. The size of matching material caps 804 and their positions are optimized through simulations in some way that there is low coupling between adjacent antennas and minimum insertion loss of the matching material. This structure can rotate approximately ±11.25 degrees. This rotation extends the spatial sampling of electromagnetic fields and decreases ill-posed situations in inverse tomography problems. FIGS. 10B and 10C illustrate an example of a mechanical structure. This example requires space due to the arms 1074. In this example of a structure there are four arms 1074, and each arm 1074 has at least one sensor 800.

FIG. 10D illustrates in different views an example of another mechanical structure 1080 for a brain scanner, in accordance with some embodiments. The structure 1080 is a modification of the mechanical system shown in FIGS. 10B and 10C. The structure 1080 has a compact structure. In this mechanism, the sensor 1084 is guided by the arm 1081 on the rail 1082 to the patient's head. In this mechanism, the tensile force of an elastic tube 1085 causes the arm 1081 to move in the direction of the rail 1082, and the sensor 1084 moves closer to the center of the circle in the direction of the circle radius. With the vertical movement of the nut 1083, the armrest moves and causes the tip of the arm 1081 to move. The upper arm touches an edge on the cover 1086 and slides on the edge. So, by moving the nut 1083, the lower part of the arm 1081 moved exactly on the rail 1082. In this version, the sensor 1084 moves closer or farther from the patient's head. In some embodiments, the controller 416 may be used actuate the movement described above. The rail 1082 can be in any place in the head scanner. The arm restriction can be in one or multiple locations. The arms 1081 can be one or multiple parts.

FIG. 10E illustrates in different views the example of the mechanical structure 1080 for a brain scanner in more detail, in accordance with some embodiments. The arm restriction can be transferred to lower parts as shown in FIG. 10E. The upper arm 1081 may be restricted to rotate only with the rotational joint in cover 1086, and the degree of freedom may be transferred to the lower arm 1081. Also, the sensor 1084 may be constrained to move in the direction of the rail 1082 and only moves towards or away from the patient's head with a translation motion without rotation. In these configurations at least one arm with may have at least one sensor. The rotation of screw 1087 can be performed manually or by a controlled motor such as a stepper motor. The position of each sensor may be read by some position sensors such as camera or laser sensors. The Microwave, RF section 414, and control sections 416 may be integrated to the head scanner. The entire system can be installed on a holder with rotational movement to adjust around the human head. The insides of cover 1086 and 1083 may be covered by RF absorbers to eliminate the reflection of electromagnetic waves from inside parts.

Figure 10F:
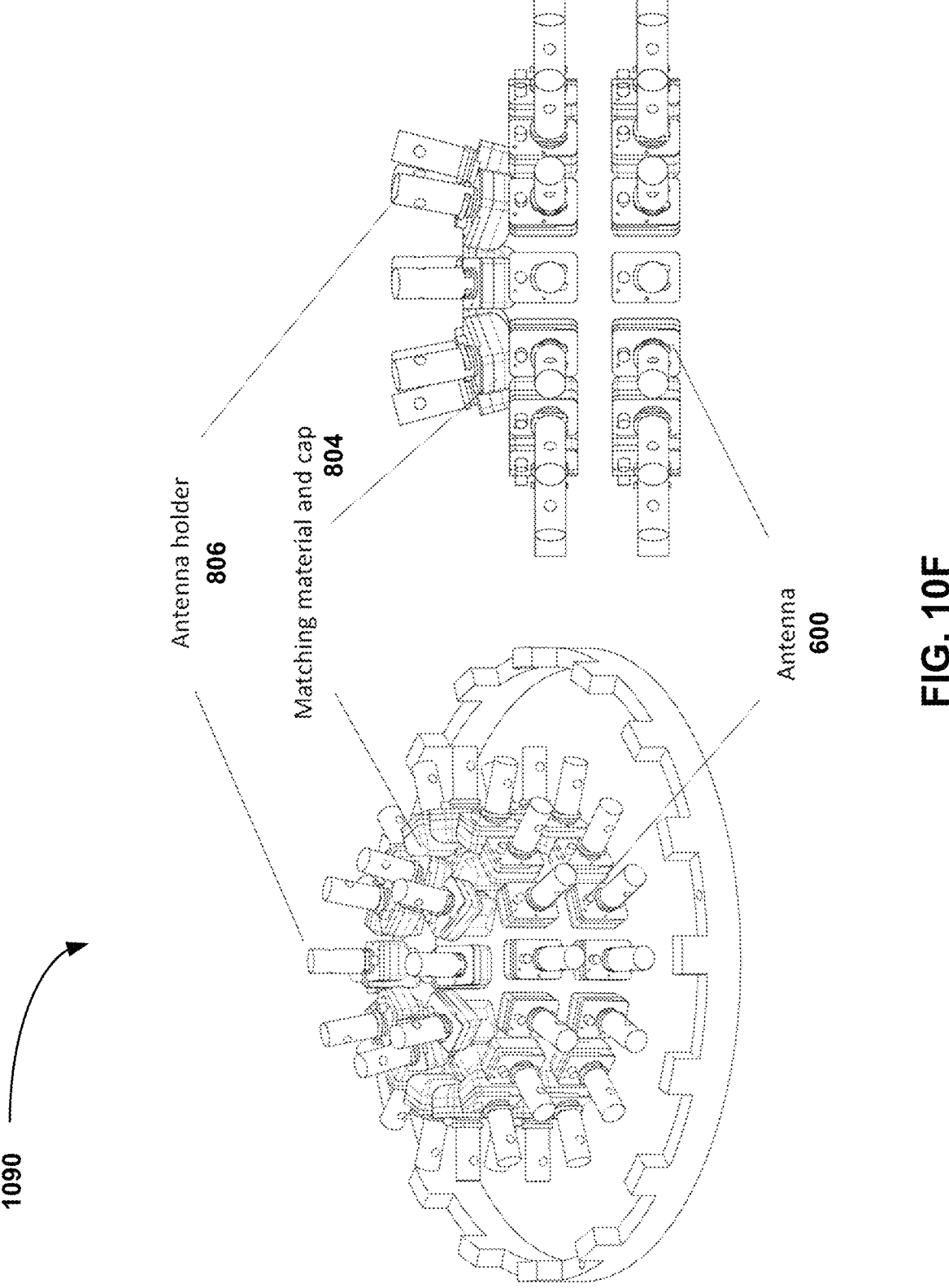
FIG. 10F illustrates in different views an example of a three dimensional (3D) mechanical structure for a brain scanner, in accordance with some embodiments.

FIG. 10F illustrates in different views an example of a three dimensional (3D) mechanical structure 1090 for a brain scanner, in accordance with some embodiments. The structure 1090 includes antenna 600, antenna holders 806 and matching material and caps 804. Both 2D and 3D configurations are possible with this design. The arrangement of sensors 800 mounted on the arms of the head scanner can be easily changed and the number of sensors and the number of rows of sensors can be increased. In addition to the sensor array around the head, a patch of sensors can also be placed above the head. The sensors on the top section can be fixed or have some movement for a better fit on the human head.

Figure 11:
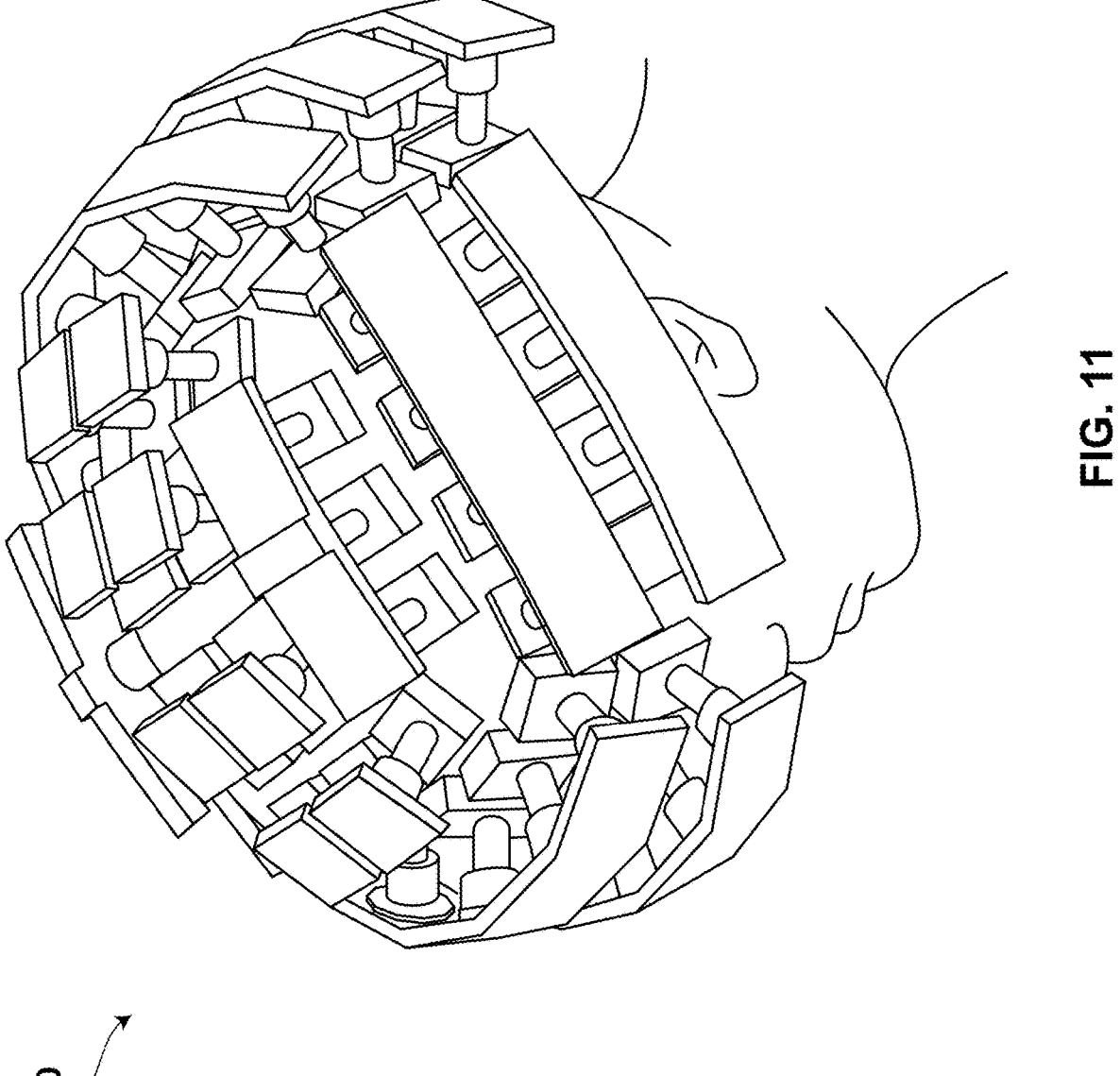
FIG. 11 illustrates another example of an antenna structure, in accordance with some embodiments.

FIG. 11 illustrates another example of an antenna structure 1100, in accordance with some embodiments. The structure 1000 can be extended to 3D structure 1100 by adding more antennas around the human head as shown in FIG. 11. In this structure, multiple antennas are put in the head scanner around human head. This structure 1100 can be calibrated for different human head sizes.

Figure 12A:
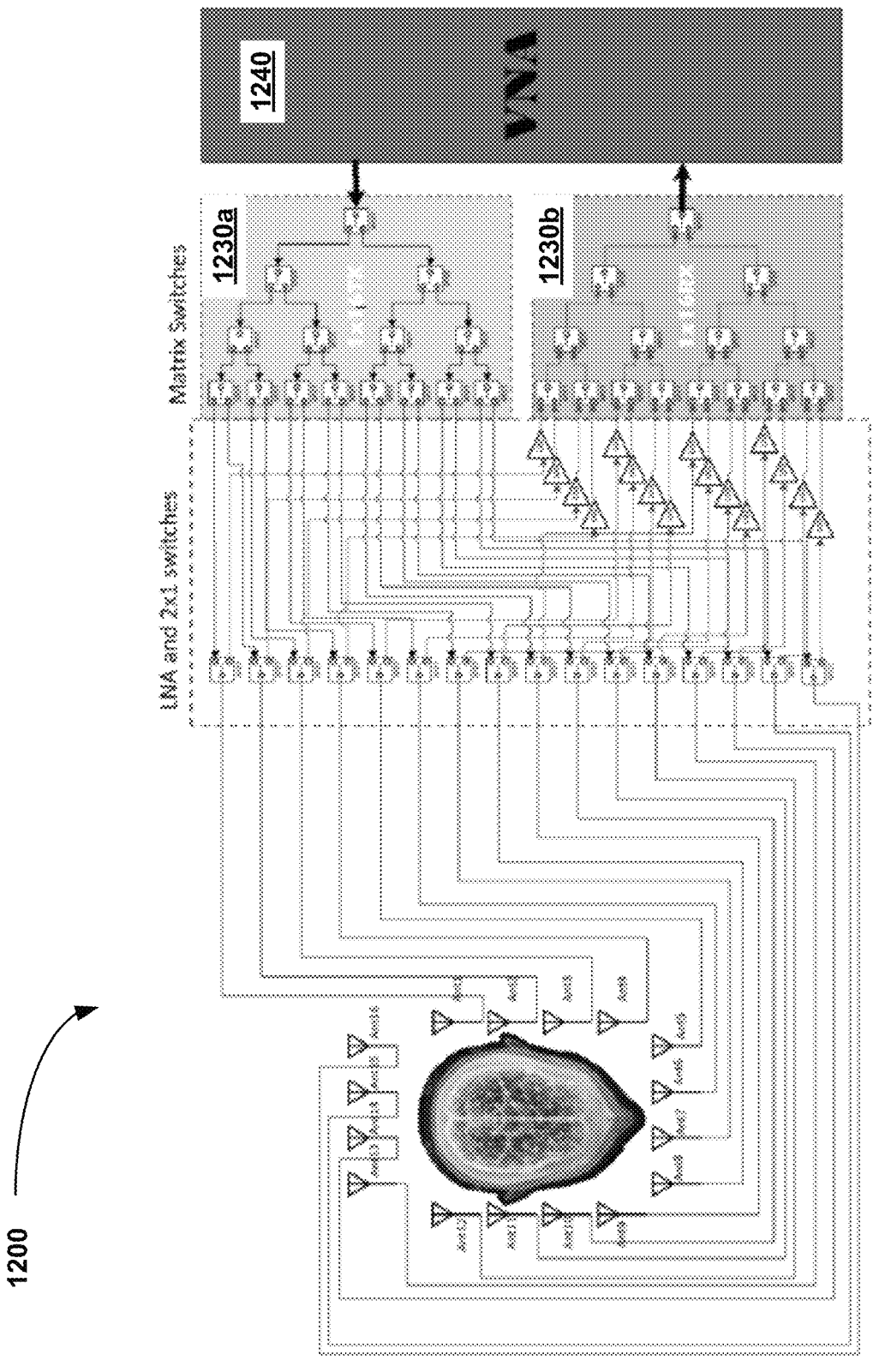
FIG. 12A illustrates, in a schematic, an example of a microwave circuit structure, in accordance with some embodiments.
Figure 12B:
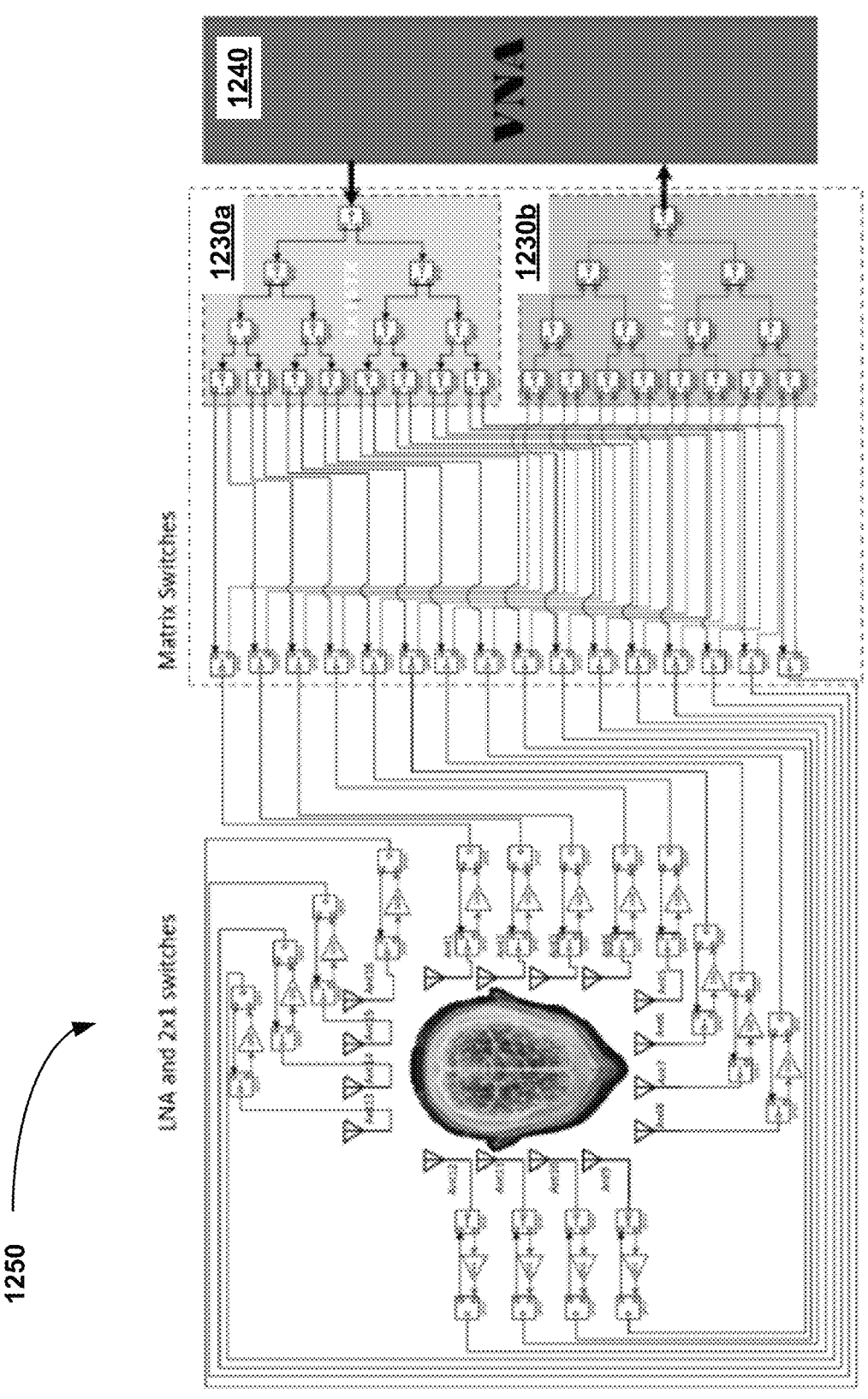
FIG. 12B illustrates, in a schematic, another example of a microwave circuit structure, in accordance with some embodiments.

FIG. 12A illustrates, in a schematic, an example of a microwave circuit structure 1200, in accordance with some embodiments. The microwave circuit design is based on a vector network analyzer (VNA) 1240 and a combination of switches and LNA 722. In this example, one structure has 16 PCB boards, each having a LNA and one 2×1 switch 724, 226. The output of these boards goes to two 16×1 matrix switches 1230a, 1230b as shown in FIG. 12A. In this structure 1200, the antenna board is a 2-layer PCB. FIG. 12B illustrates, in a schematic, another example of a microwave circuit structure 1250, in accordance with some embodiments. The LNA 722 and two 2×1 724, 726 switches may be considered in the antenna board as shown in FIG. 12B. Each antenna is connected to the matrix switches boards with just one cable. This design gives us maximum SNR and decreases manufacturing costs. The microwave structure 1250 is more compact and scalable compared to structure 1200.

In some embodiments, there may be multiple sensors around the human head in a 3D format. In some embodiments, the sampling time for scattering parameters may be approximately 25 seconds if each measurement takes 10 milliseconds (ms). The control section of the scanner may select the proper switching path and reads scattering parameters each time. Other timing combinations are possible.

In some designs the number of antennas may be numerous and it takes a lot of time for reading scattering parameters. In this situation, human head position may change and cause error. In some other designs, scattering parameters are calculation based on heterodyne transceivers and scattering parameters extracted from time domain responses. In these structures, antenna reflections are not calculated and considered in imaging algorithms which increases the ill-posed condition of inverse problem.

Electromagnetic tomography image processing is an iterative process including a forward algorithm and an inverse algorithm as shown in FIG. 3. The forward method solves electromagnetic fields in the imaging area with specific dielectric properties. The linear forward methods such as the Born method causes error and decreases image resolution. On the other hand, non-linear numerical solutions are accurate but they are slow. Finite-Difference Time-Domain (FDTD) is a numerical promising method for solving electromagnetic equations and calculating electromagnetic fields. This numerical method can be implemented on GPU with parallel processing methods to decrease processing time. In each iteration, new scattering parameters are calculated and used in a cost function. If the cost function does not meet a specific tolerance, an inverse algorithm is applied to calculate new permittivities and conductivities for different imaging areas. This process continues until a number of iterations or cost function reaches an acceptable value.

The inverse algorithms can be based on exact algorithms or stochastic optimization methods. The exact solutions such as gradient descent method have ill-posed conditions and are very slow especially for 3D scanner models. The stochastic optimization algorithms such as Simulated Annealing (SA), Genetic Algorithm (GA), Sequential Quadratic Programming (SQP), Particle Swarm Optimization (PSO) can escape from local minimums. While the stochastic algorithms do not guarantee exact optimality, but a fair solution may be obtained in a shorter execution time with acceptable image resolution.

Figure 13A:
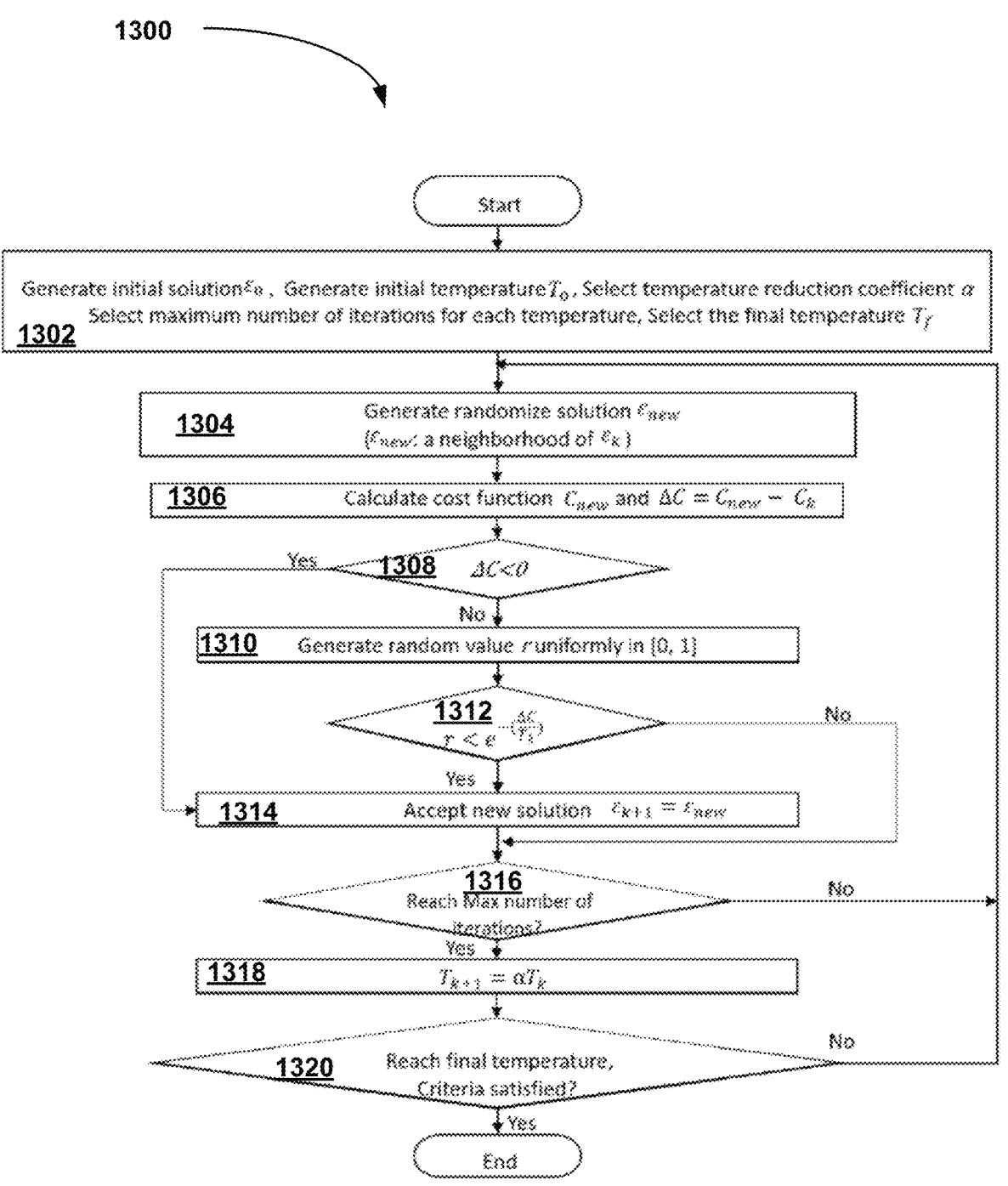
FIG. 13A illustrates, in a flowchart, an example of a method of simulated annealing, in accordance with some embodiments.
Figure 13B:
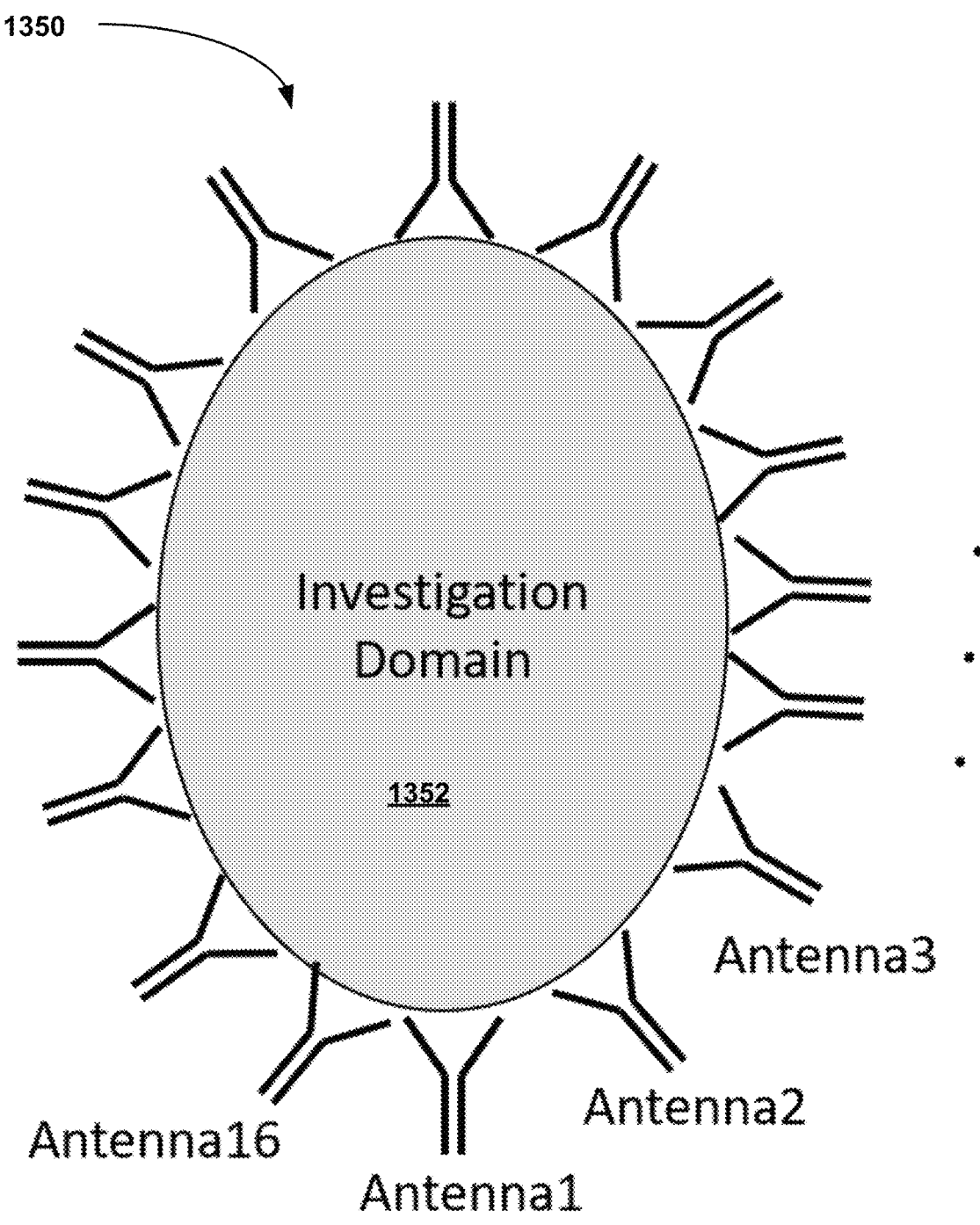
FIG. 13B illustrates, in a schematic, an example of a homogenous EM tomography system, in accordance with some embodiments.

FIG. 13A illustrates, in a flowchart, an example of a method 1300 of simulated annealing, in accordance with some embodiments. In some embodiments, the Inverse EM scattering problem may be solved using the SA method 1300. FIG. 13B illustrates, in a schematic, an example of a homogenous EM tomography system 1350, in accordance with some embodiments. There is an investigation domain 1352 that includes the total imaging area. The transmitter and receiver antennas are located outside the investigation domain. In the inverse problems of EM scattering, the objective is to find the permittivity profile of the investigation domain. The SA algorithm can be developed for both homogenous and heterogonous domains.

The measured scattering parameters or simulation values are inputs of the method 1300. Since the unknown parameters are more than known ones, there is no straight answer for this problem and the SA method 1300 may be chosen as a random solution generator to reach the best solution.

In this approach, first the initial solution $\varepsilon_0$, the initial temperature $T_0$, the final temperature $T_f$, the temperature reduction coefficient, and maximum iteration may be generated 1302. In each iteration 1304 to 1320, the scattering parameters of the estimated profile may be calculated using FDTD algorithm and the cost function of the new solution is obtained by comparing with realistic data. Then a new solution may be generated that is the previous one with a little random difference, called a neighborhood.

The iteration loop may be started within the temperature loop. A randomized solution $\varepsilon_{new}$ may be generated 1304 where $\varepsilon_{new}$ is a neighborhood of $\varepsilon_k$. The cost value $C_{new}$ of new solution may be computed 1306. According to the method 1300, if the new cost value is less than previous one 1308 ($\Delta C < 0$, where $\Delta C = C_{new} - C_k$), the new solution $\varepsilon_{new}$ will be accepted as a better solution ($\varepsilon_{k+1} = \varepsilon_{new}$). Otherwise, a random number r uniformly in the continuous domain [0, 1] may be generated 1310 and the new solution $\varepsilon_{k+1}$ will be accepted 1314 with an acceptance probability function 1312, where $$r < \varepsilon^{-\frac{\Delta C}{T_k}}.$$

If the acceptance probability function is not accepted, and the maximum number of iterations has not been reached 1316, then steps 1304 to 1316 may repeat. If the maximum number of iterations has been reached 1316 then another temperature is selected 1318 where $T_{k+1} = \alpha T_k$.

The iteration loop 1304 to 1320 may be repeated until the maximum number of iterations and it reaches to the final temperature 1320. The last solution obtained using this method 1300 is the optimized one.

In some embodiments, a patch antenna is provided with a tunable structure and optimized matching material cap. This provides low matching material loss, low antenna coupling, less required dynamic range, high SNR, and a higher, relatively fair and proper, resolution.

In some embodiments, a FDTD method is provided (forward), and a Simulated Annealing (SA) method is provided (inverse). The SA method is relatively fast and achieves relatively fair and proper resolution.

Figure 14:
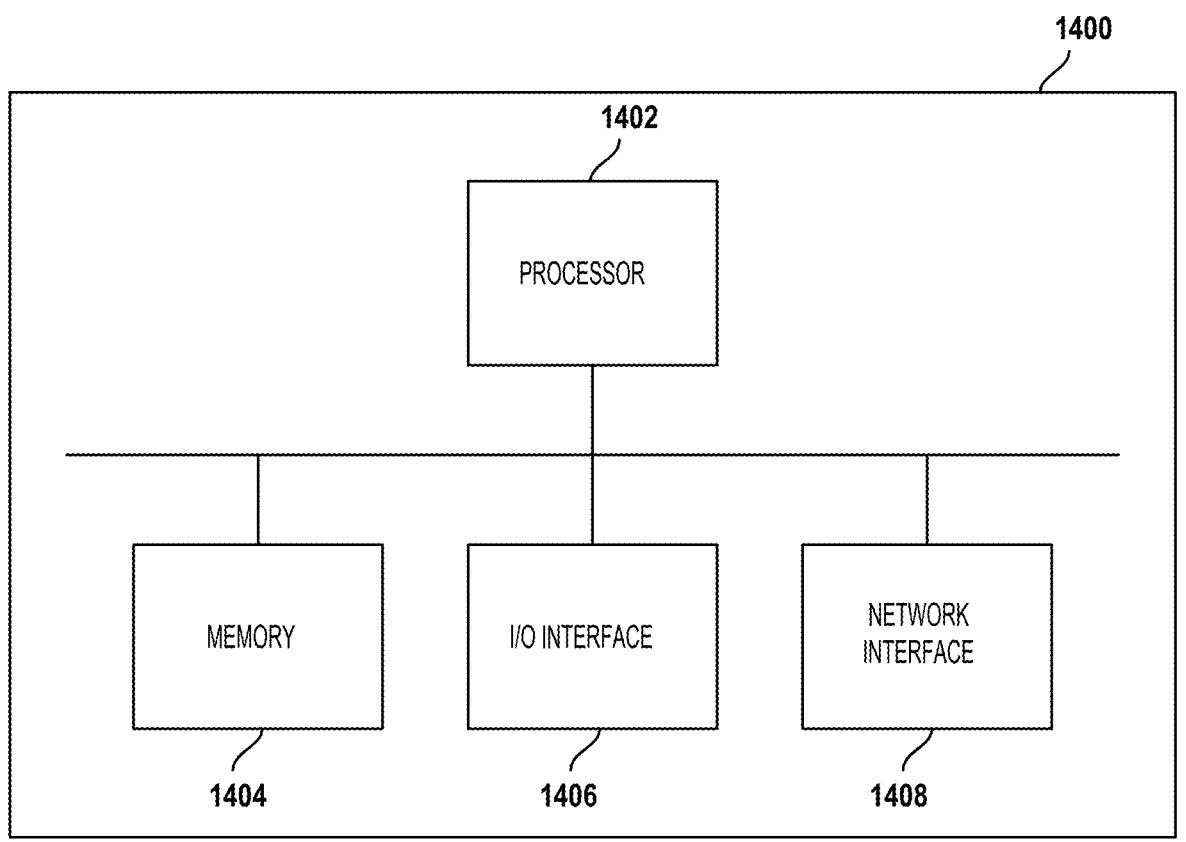
FIG. 14 is a schematic diagram of a computing device such as a server or other computer in a device.

FIG. 14 is a schematic diagram of a computing device 1400 such as a server or other computer in a device. As depicted, the computing device includes at least one processor 1402, memory 1404, at least one I/O interface 1406, and at least one network interface 708.

Processor 1402 may be an Intel or AMD×86 or ×64, PowerPC, ARM processor, or the like. Memory 1404 may include a suitable combination of computer memory that is located either internally or externally such as, for example, random-access memory (RAM), read-only memory (ROM), compact disc read-only memory (CDROM).

Each I/O interface 1406 enables computing device 1400 to interconnect with one or more input devices, such as a keyboard, mouse, camera, touch screen and a microphone, or with one or more output devices such as a display screen and a speaker.

Each network interface 1408 enables computing device 1400 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX, 5G), SS7 signaling network, fixed line, local area network, wide area network, and others.

The foregoing discussion provides example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification.

As can be understood, the examples described above and illustrated are intended to be exemplary only.

What is claimed is:

1. An electromagnetic head imaging system comprising:
an antenna chamber shaped to receive a subject head;
a plurality of sensor assemblies disposed within the antenna chamber, each sensor assembly movable around at least a portion of the subject head to be positioned opposite to another sensor assembly, each sensor assembly comprising at least one antenna;
at least one processor configured to:
move at least one sensor assembly of the plurality of sensor assemblies to a series of different positions around the subject head;
at each position of the series of different positions around the subject head, obtain electromagnetic field measurements at at least one pair of opposing sensor assemblies; and
determine scattering parameters based on the electromagnetic field measurements obtained from the at least one pair of opposing sensor assemblies in each position of the series of different positions around the subject head; and
generate an image of the subject head based on the scattering parameters associated with the series of different positions around the subject head; and
at least one arm, one or more sensor assemblies of the plurality of sensor assemblies being disposed on each arm of the at least one arm, each arm of the at least one arm being movable to move the one or more sensor assemblies disposed thereon;
wherein the subject head defines a longitudinal axis, and the system further comprises:
at least a first motor operable to adjust a roll angle of the at least one arm about the longitudinal axis and a second motor operable to adjust a pitch angle of the at least one arm about the longitudinal axis; and
a rail mechanism within the antenna chamber, the at least one arm being moveably coupled to the rail mechanism, the one or more sensor assemblies disposed on the at least one arm moving radially about the longitudinal axis when the at least one arm moves along the rail mechanism.

2. The electromagnetic head imaging system of claim 1, wherein the sensor assembly comprises a plurality of layers, the at least one antenna being disposed within an antenna layer of the plurality of layers.

3. The electromagnetic head imaging system of claim 2, wherein each sensor assembly further comprises at least one matching material configured to couple the at least one antenna to the subject head, the at least one matching material having dielectric properties similar to an average subject head.

4. The electromagnetic head imaging system of claim 3, wherein the at least one matching material is disposed within a matching material layer of the plurality of layers, the matching material layer being in contact with the antenna layer.

5. The electromagnetic head imaging system of claim 2, wherein each sensor assembly further comprises a plurality of switches configured to operate the at least one antenna as either a transmitter or a receiver.

6. The electromagnetic head imaging system of claim 1, wherein each sensor assembly further comprises at least one amplifier configured to amplify an electromagnetic signal received by the at least one antenna.

7. The electromagnetic head imaging system of claim 6, wherein the plurality of switches and the at least one amplifier are disposed within a signal processing layer of the plurality of layers, the signal processing layer being in contact with the antenna layer.

8. The electromagnetic head imaging system of claim 6, wherein the at least one antenna layer is disposed on a first printed circuit board and the plurality of switches and the at least one amplifier are disposed on a second printed circuit board separate from the first printed circuit board.

9. The electromagnetic head imaging system of claim 1, wherein the at least one processor being configured to, at each position of the series of different positions, obtain electromagnetic field measurements at at least one pair of opposing sensor assemblies comprises the at least one processor being configured to:

transmit, from a first sensor assembly of the at least one pair of opposing sensors, at least one electromagnetic signal to a second sensor assembly of the at least one pair of opposing sensors;

receive, at the first sensor assembly, at least one electromagnetic field measurement indicative of a parameter of reflection of the transmission from the first sensor; and receive, at the second sensor assembly, at least one electromagnetic field measurement indicative of a parameter of transmission of the transmission from the first sensor.

10. The electromagnetic head imaging system of claim 9, wherein the at least one processor is further configured to:

transmit, from the second sensor assembly, at least one electromagnetic signal to the first sensor assembly;

receive, at the second sensor assembly, at least one electromagnetic field measurement indicative of a parameter of reflection of the transmission from the second sensor assembly; and receive, at the first sensor assembly, at least one electromagnetic field measurement indicative of a parameter of transmission of the transmission from the second sensor assembly.

11. The electromagnetic head imaging system of claim 1, wherein the at least one processor is configured to, for each sensor assembly, transmit at least one electromagnetic signal to every other sensor assembly of the plurality of sensor assemblies.

12. The electromagnetic head imaging system of claim 1, wherein the at least one processor is configured to calibrate the plurality of sensor assemblies prior to moving at least one sensor assembly of the plurality of sensor assemblies to a series of different positions around the subject head.

13. The electromagnetic head imaging system of claim 1, wherein the at least one processor being configured to, generate an image of the subject head based on the scattering parameters associated with the series of different positions comprises the at least one processor being configured to:

generate estimated scattering parameters for a plurality of areas within the antenna chamber around the subject head based on an estimated permittivity and an estimated conductivity for the plurality of areas;

compare the estimated scattering parameters with the scattering parameters obtained from measurement to determine whether the estimated scattering parameters have converged with the scattering parameters obtained from measurement; and

upon determining that the estimated scattering parameters have converged with the scattering parameters obtained from measurement, generate the image of the subject head; otherwise upon determining that the estimated scattering parameters have not converged with the scattering parameters obtained from measurement, re-generate the estimated permittivity and an estimated conductivity until the estimated scattering parameters converge with the scattering parameters obtained from measurement.

14. The electromagnetic head imaging system of claim 13, wherein the at least one processor being configured to generate estimated scattering parameters for a plurality of areas within the antenna chamber around the subject head based on an estimated permittivity and an estimated conductivity for the plurality of areas comprises the at least one processor being configured to:

determine an estimated electric field intensity and an estimated magnetic field intensity for each area of the plurality of areas based on the estimated permittivity and the estimated conductivity for that area; and determine the estimated scattering parameters for each area of the plurality of areas based on the estimated electric field intensity and the estimated magnetic field intensity for that area.

15. The electromagnetic head imaging system of claim 14, wherein the at least one processor is configured to select predefined values as an initial permittivity and an initial conductivity for each area of the plurality of areas.

16. The electromagnetic head imaging system of claim 13, wherein the at least one processor being configured to re-generate the estimated permittivity and an estimated conductivity until the estimated scattering parameters converge with the scattering parameters obtained from measurement comprises the at least one processor being configured to:

select a subsequent permittivity within a pre-defined range of the estimated permittivity prior to being re-generated;

determine a subsequent conductivity based on the subsequent permittivity; and use an optimization algorithm to determine whether to adopt the subsequent permittivity and the subsequent conductivity as the estimated permittivity and an estimated conductivity.

17. A method of generating an electromagnetic image of a subject head, the method comprising:

receiving the subject head within an antenna chamber;

moving at least one sensor assembly of a plurality of sensor assemblies to a series of different positions around the subject head, wherein the at least one sensor assembly is disposed on at least one arm and the subject head defines a longitudinal axis, and wherein at least a first motor operates to adjust a roll angle of the at least one arm about the longitudinal axis and a second motor operates to adjust a pitch angle of the at least one arm about the longitudinal axis; and operating at least one processor to:

obtain electromagnetic field measurements at at least one pair of opposing sensor assemblies when the at least one sensor assembly is at each position of the series of different positions around the subject head;

determine scattering parameters based on the electromagnetic field measurements; and generate an image of the subject head based on the scattering parameters associated with the series of different positions around the subject head.

* * * * *